(12) United States Patent
Panesar et al.

(10) Patent No.: US 12,403,282 B2
(45) Date of Patent: Sep. 2, 2025

(54) METHODS OF MAKING SLEEVED HYDROPHILIC CATHETER ASSEMBLIES

(71) Applicant: Hollister Incorporated, Libertyville, IL (US)

(72) Inventors: Satwinder S. Panesar, Foxford (IE); David J. Farrell, Ballina (IE); Shane O'Malley, Ballina (IE); Patrick Boland, Easkey (IE); Brendan J. Heneghan, Westport (IE); Horacio Montes De Oca, Ballina (IE); Michael G. Murray, Ballina (IE); John Joe McDermott, Newport (IE); Damien Biggins, Hollymount (IE); Ryan Hutchinson, Libertyville, IL (US); Charlotte Weir, Ballina (IE); Richard Meaney, Westport (IE); Robert A. Greynolds, Northbrook, IL (US); Christina Augustyn, Chicago, IL (US); George J. Cisko, Spring Grove, IL (US); Adam J. Foley, Swords (IE); Martin Bruggernan, Mountrath (IE)

(73) Assignee: Hollister Incorporated, Libertyville, IL (US)

( * ) Notice: Subject to any disclaimer, the term of this patent is extended or adjusted under 35 U.S.C. 154(b) by 1059 days.

(21) Appl. No.: 17/055,967

(22) PCT Filed: May 17, 2019

(86) PCT No.: PCT/US2019/032892
§ 371 (c)(1),
(2) Date: Nov. 16, 2020

(87) PCT Pub. No.: WO2019/222644
PCT Pub. Date: Nov. 21, 2019

(65) Prior Publication Data
US 2021/0260332 A1    Aug. 26, 2021

Related U.S. Application Data

(60) Provisional application No. 62/842,318, filed on May 2, 2019, provisional application No. 62/821,268, filed
(Continued)

(51) Int. Cl.
*A61M 25/00*      (2006.01)
*A61L 29/04*      (2006.01)
(Continued)

(52) U.S. Cl.
CPC ....... *A61M 25/0009* (2013.01); *A61L 29/043* (2013.01); *A61L 29/143* (2013.01);
(Continued)

(58) Field of Classification Search
CPC ............ A61M 25/0009; A61M 25/002; A61M 25/0111; A61L 29/043; A61L 29/143;
(Continued)

(56) References Cited

U.S. PATENT DOCUMENTS 4,026,296 A     5/1977  Stoy et al.
4,692,154 A *   9/1987  Singery .............. A61M 25/0111
                                                   604/271
(Continued)

FOREIGN PATENT DOCUMENTS

EP      1131112 B1   2/2003
EP      1312385 B1   2/2006
(Continued)

OTHER PUBLICATIONS

International Search Report from Int. App. No. PCT/US2019/032892 dated Mar. 9, 2019.
(Continued)

*Primary Examiner* — Nicholas J. Weiss
*Assistant Examiner* — Gabriella E Burnette
(74) *Attorney, Agent, or Firm* — Cook Alex Ltd.

(57) ABSTRACT

Methods of making sleeved hydrophilic urinary catheters.

18 Claims, 17 Drawing Sheets

Related U.S. Application Data on Mar. 20, 2019, provisional application No. 62/821,284, filed on Mar. 20, 2019, provisional application No. 62/770,275, filed on Nov. 21, 2018, provisional application No. 62/739,449, filed on Oct. 1, 2018, provisional application No. 62/699,993, filed on Jul. 18, 2018, provisional application No. 62/672,755, filed on May 17, 2018.

(51) Int. Cl.
  *A61L 29/14* (2006.01)
  *A61M 25/01* (2006.01)
  *B65D 81/22* (2006.01)

(52) U.S. Cl.
  CPC ......... *A61L 29/146* (2013.01); *A61M 25/002* (2013.01); *A61M 25/0111* (2013.01); *A61L 2400/10* (2013.01); *B65D 81/22* (2013.01)

(58) Field of Classification Search
  CPC .... A61L 29/146; A61L 2400/10; A61L 29/14; B65D 81/22
  See application file for complete search history.

(56) References Cited

U.S. PATENT DOCUMENTS

| | | |
|---|---|---|
| 4,906,237 A | 3/1990 | Johansson et al. |
| 5,562,652 A | 10/1996 | Davis |
| 5,576,072 A | 11/1996 | Hostettler et al. |
| 5,616,119 A | 4/1997 | Davis |
| 5,623,043 A * | 4/1997 | Fost .............. C08G 77/388 528/25 |
| 5,876,663 A | 3/1999 | Laroussi |
| 6,090,075 A * | 7/2000 | House ............. A61M 25/0017 604/523 |
| 6,120,904 A | 9/2000 | Hostettler et al. |
| 6,270,902 B1 | 8/2001 | Tedeschi et al. |
| 6,528,544 B2 | 3/2003 | Stem et al. |
| 6,629,961 B1 | 10/2003 | Israelsson et al. |
| 6,634,498 B2 | 10/2003 | Kayeroed et al. |
| 6,848,574 B1 | 2/2005 | Israelsson et al. |
| 6,923,936 B2 | 8/2005 | Swanson et al. |
| 6,986,868 B2 | 1/2006 | Madsen |
| 7,022,651 B1 | 4/2006 | Lightcap, Jr. et al. |
| 7,066,912 B2 | 6/2006 | Nestenborg et al. |
| 7,282,165 B2 | 10/2007 | Williams, III et al. |
| 7,476,223 B2 | 1/2009 | McBride |
| 7,569,155 B2 | 8/2009 | Schaefer |
| 7,833,475 B2 | 11/2010 | Madsen |
| 8,133,435 B2 | 3/2012 | Reynolds et al. |
| 8,177,774 B2 | 5/2012 | House |
| 8,267,919 B2 | 9/2012 | Utas et al. |
| 8,608,689 B2 | 12/2013 | Scheller et al. |
| 8,703,048 B2 | 4/2014 | Nielsen et al. |
| 8,747,882 B2 | 6/2014 | Utas et al. |
| 8,747,911 B2 | 6/2014 | Gupta et al. |
| 8,871,869 B2 | 10/2014 | Dias et al. |
| 8,998,882 B2 | 4/2015 | Knapp et al. |
| 9,028,858 B2 | 5/2015 | Nielsen et al. |
| 9,138,510 B2 | 9/2015 | Madsen |
| 9,192,741 B1 | 11/2015 | Najibi |
| 9,220,866 B2 | 12/2015 | Van Groningen et al. |
| 9,408,946 B2 | 8/2016 | Utas et al. |
| 9,610,384 B2 | 4/2017 | Belt et al. |
| 9,801,979 B2 | 10/2017 | Utas et al. |
| 9,872,970 B2 | 1/2018 | Schønfeldt |
| 10,112,031 B2 | 10/2018 | Matthlassen |
| 10,245,355 B2 | 4/2019 | Ingber et al. |
| 10,398,161 B2 | 9/2019 | Ame et al. |
| 10,561,817 B2 | 2/2020 | Hannon et al. |
| 11,420,017 B2 * | 8/2022 | Hilton .................. A61M 39/10 |
| 2002/0045049 A1 | 4/2002 | Madsen |
| 2002/0120333 A1 | 8/2002 | Keogh et al. |
| 2003/0065292 A1 | 4/2003 | Darouiche et al. |
| 2003/0124080 A1 | 7/2003 | Kawam et al. |
| 2003/0219475 A1 | 11/2003 | Truong-Le |
| 2004/0074794 A1 | 4/2004 | Conway et al. |
| 2004/0256264 A1 | 12/2004 | Israelsson et al. |
| 2005/0015076 A1 | 1/2005 | Glebmeyer et al. |
| 2005/0055044 A1 | 3/2005 | Kangas |
| 2005/0137582 A1 | 6/2005 | Kull-Osterlin et al. |
| 2005/0214376 A1 | 9/2005 | Faure et al. |
| 2006/0163097 A1 | 7/2006 | Murray et al. |
| 2007/0088330 A1 * | 4/2007 | House ............. A61M 25/0111 604/327 |
| 2007/0239107 A1 | 10/2007 | Lundberg et al. |
| 2007/0244449 A1 | 10/2007 | Najafi et al. |
| 2008/0142038 A1 | 6/2008 | Kunzler et al. |
| 2009/0012208 A1 | 1/2009 | Madsen et al. |
| 2009/0041727 A1 | 2/2009 | Suzuki et al. |
| 2009/0171317 A1 | 7/2009 | Versi |
| 2009/0221989 A1 | 9/2009 | Najafi et al. |
| 2009/0240214 A1 | 9/2009 | Conway et al. |
| 2010/0166809 A1 | 7/2010 | Northey et al. |
| 2010/0215643 A1 | 8/2010 | Clevenger et al. |
| 2010/0258568 A1 | 10/2010 | Frederiksen et al. |
| 2011/0114520 A1 | 5/2011 | Matthison-Hansen |
| 2011/0150961 A1 | 6/2011 | Perry et al. |
| 2011/0230864 A1 * | 9/2011 | House ............. A61M 25/0111 604/544 |
| 2012/0207853 A1 | 8/2012 | Alimi et al. |
| 2012/0289942 A1 | 11/2012 | Becker et al. |
| 2012/0316515 A1 | 12/2012 | Terry |
| 2013/0231641 A1 * | 9/2013 | Gustavsson ......... A61M 25/013 604/544 |
| 2014/0190846 A1 | 7/2014 | Belt |
| 2014/0271351 A1 | 9/2014 | Nielsen et al. |
| 2015/0065998 A1 | 3/2015 | Nielsen et al. |
| 2015/0238726 A1 | 8/2015 | Terry |
| 2015/0264935 A1 | 9/2015 | Chang |
| 2016/0143944 A1 | 5/2016 | Panicheva et al. |
| 2016/0213880 A1 * | 7/2016 | O'Flynn ............. A61M 25/002 |
| 2017/0296609 A1 | 10/2017 | Ellington et al. |
| 2017/0312484 A1 | 11/2017 | Shipley et al. |
| 2018/0000993 A1 | 1/2018 | Zhang |
| 2018/0010038 A1 | 1/2018 | Greenhill-Hooper et al. |
| 2018/0221541 A1 | 8/2018 | Pesika et al. |
| 2018/0258363 A1 | 9/2018 | Rhodes et al. |
| 2019/0001098 A1 | 1/2019 | Utas et al. |
| 2019/0083746 A1 | 3/2019 | Murray et al. |
| 2019/0151610 A1 | 5/2019 | Fletter |
| 2019/0167849 A1 | 6/2019 | Mcburney et al. |
| 2019/0216985 A1 | 7/2019 | Mcburney et al. |
| 2019/0262647 A1 | 8/2019 | Havelka-Rivard et al. |
| 2019/0290806 A1 | 9/2019 | Farrell et al. |
| 2020/0038535 A1 | 2/2020 | Montes De Oca et al. |
| 2020/0054795 A1 | 2/2020 | Farrell et al. |
| 2020/0146871 A1 | 5/2020 | Palmer |

FOREIGN PATENT DOCUMENTS

| | | |
|---|---|---|
| EP | 1312385 B2 | 10/2009 |
| EP | 1714665 B1 | 8/2011 |
| EP | 2695636 A1 | 2/2014 |
| EP | 2550030 B1 | 4/2018 |
| EP | 3071249 B1 | 8/2018 |
| WO | 2002100455 A1 | 1/2002 |
| WO | 2005117914 A2 | 12/2005 |
| WO | 2014074141 A1 | 5/2014 |
| WO | 2016033234 A1 | 3/2016 |
| WO | 2017001830 A1 | 1/2017 |
| WO | 2018028831 A1 | 2/2018 |
| WO | 2018029279 A1 | 2/2018 |

OTHER PUBLICATIONS

International Preliminary Report on Patentability from Int. App. No. PCT/US2019/032906 dated Nov. 17, 2020.

Written Opinion of the International Search Authority from Int. App. No. PCT/US2019/032892 dated Mar. 9, 2019.

(56) References Cited

OTHER PUBLICATIONS

International Search Report from Int. App. No. PCT/US2019/032906 dated Oct. 14, 2019.
Castro, V. I., Craveiro, R., Silva, J. M., Reis, R. L., Paiva, A., & C. Duarte, A. R. (2018). Natural deep eutectic systems as alternative nontoxic cryoprotective agents. Cryobiology, 83, 15-26.
Extended European Search Report issued in European Patent App. 22211526.3-1109, dated Apr. 6, 2023.

* cited by examiner

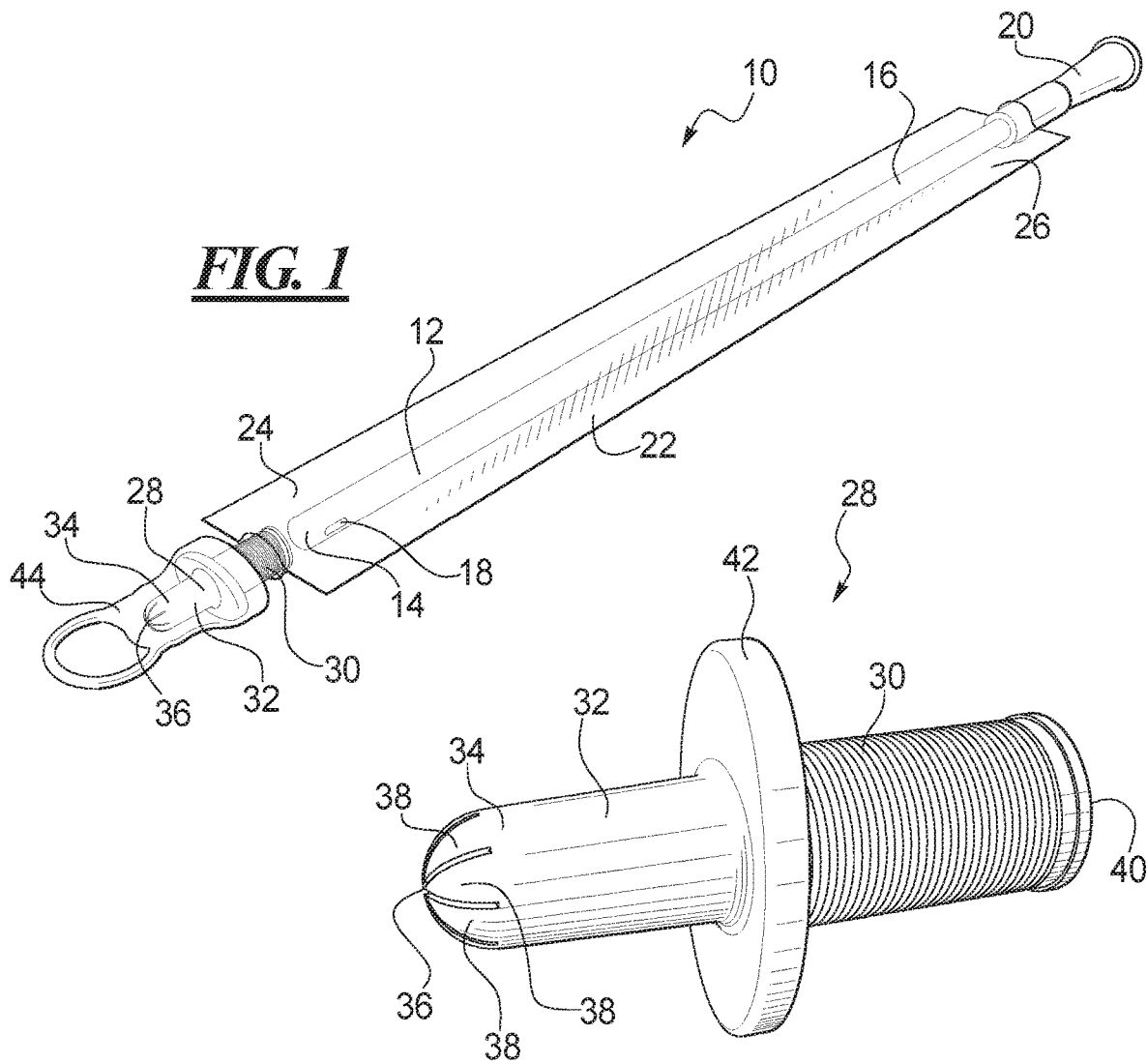
FIG. 1
FIG. 2
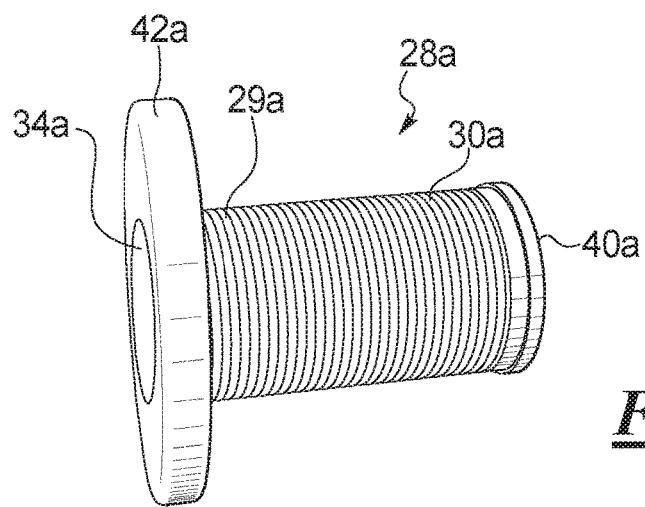
FIG. 3

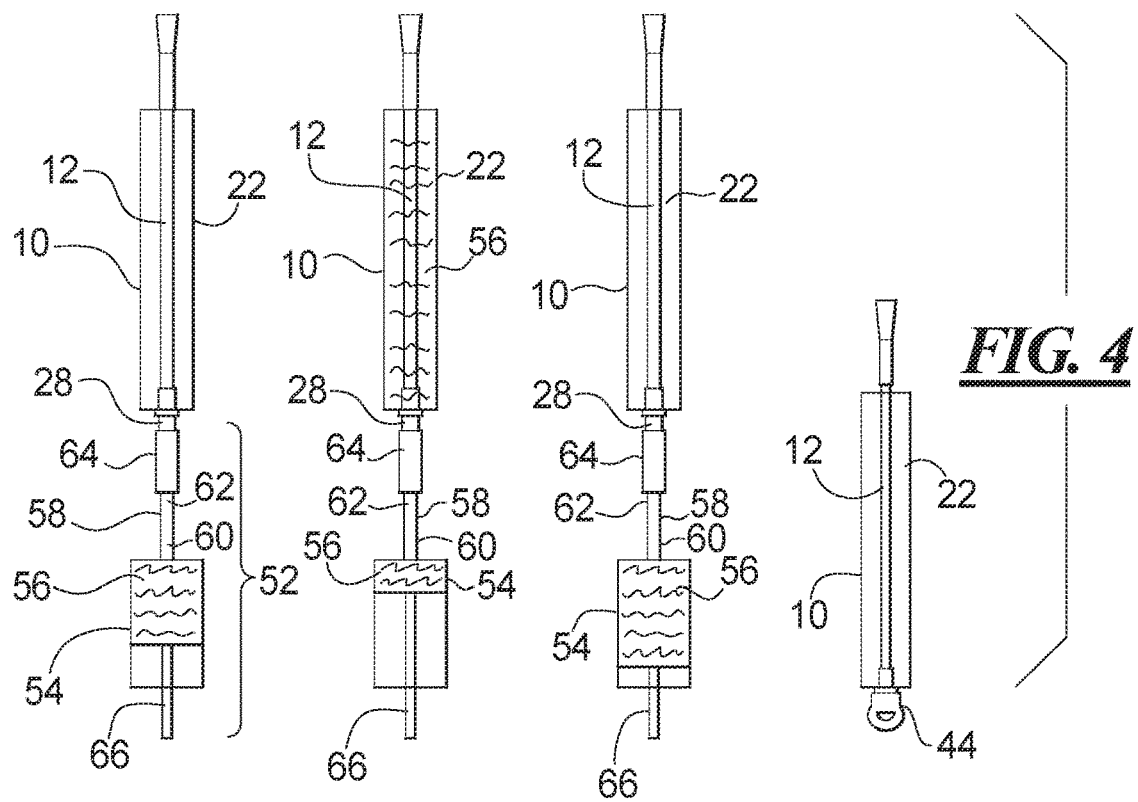
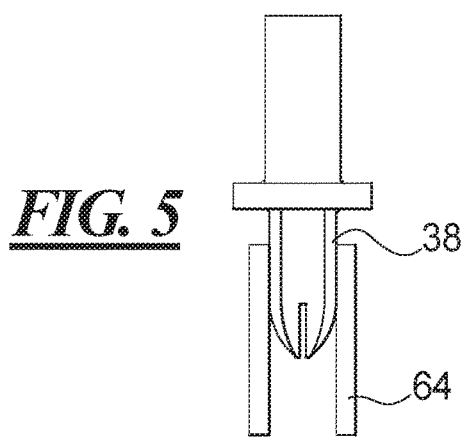
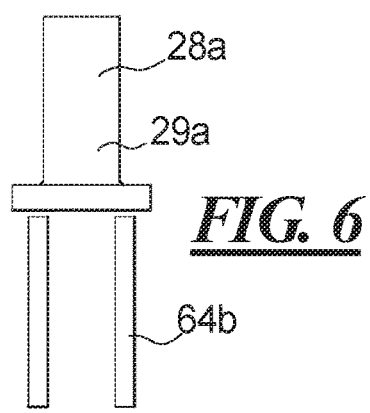
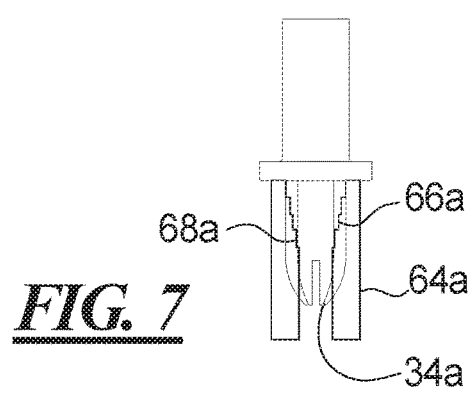
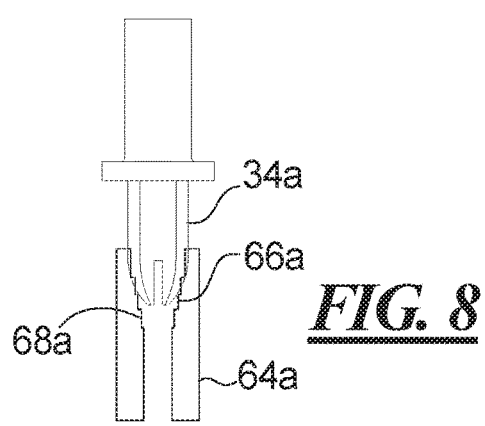

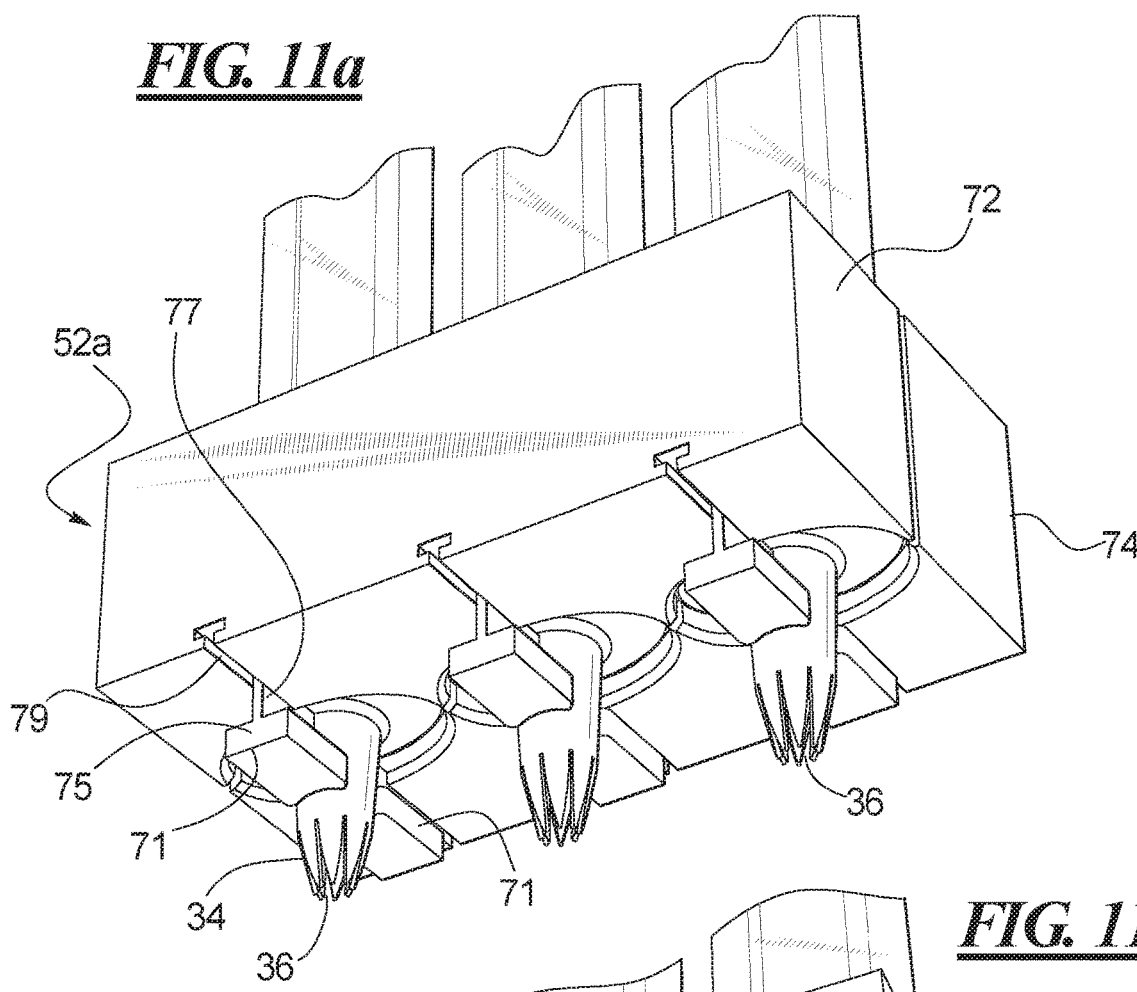
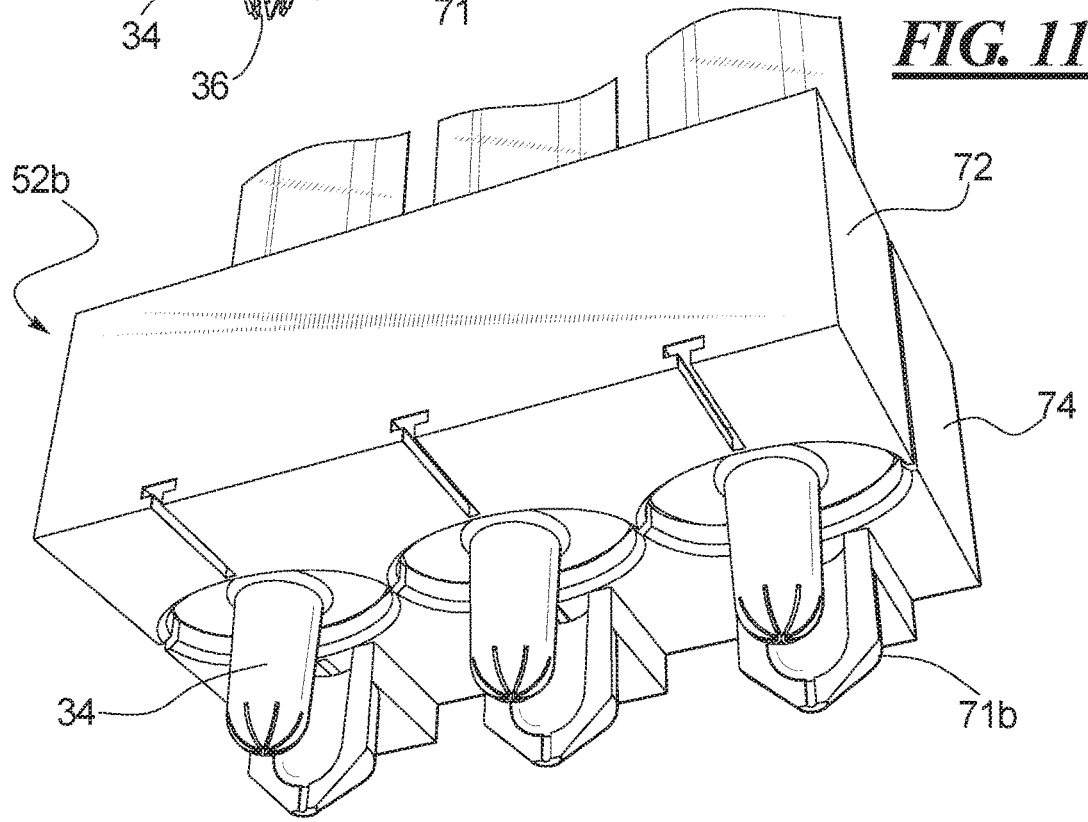

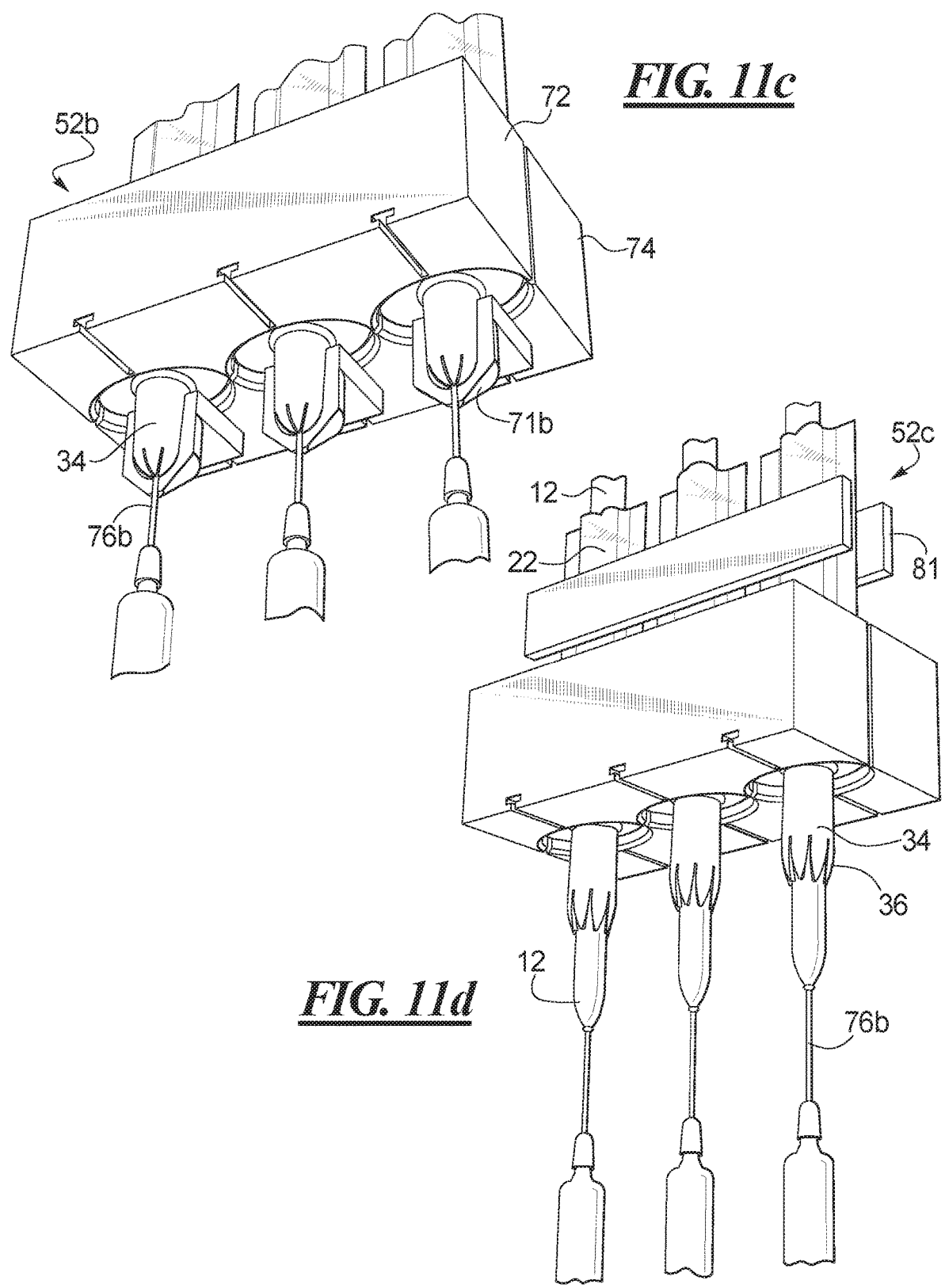

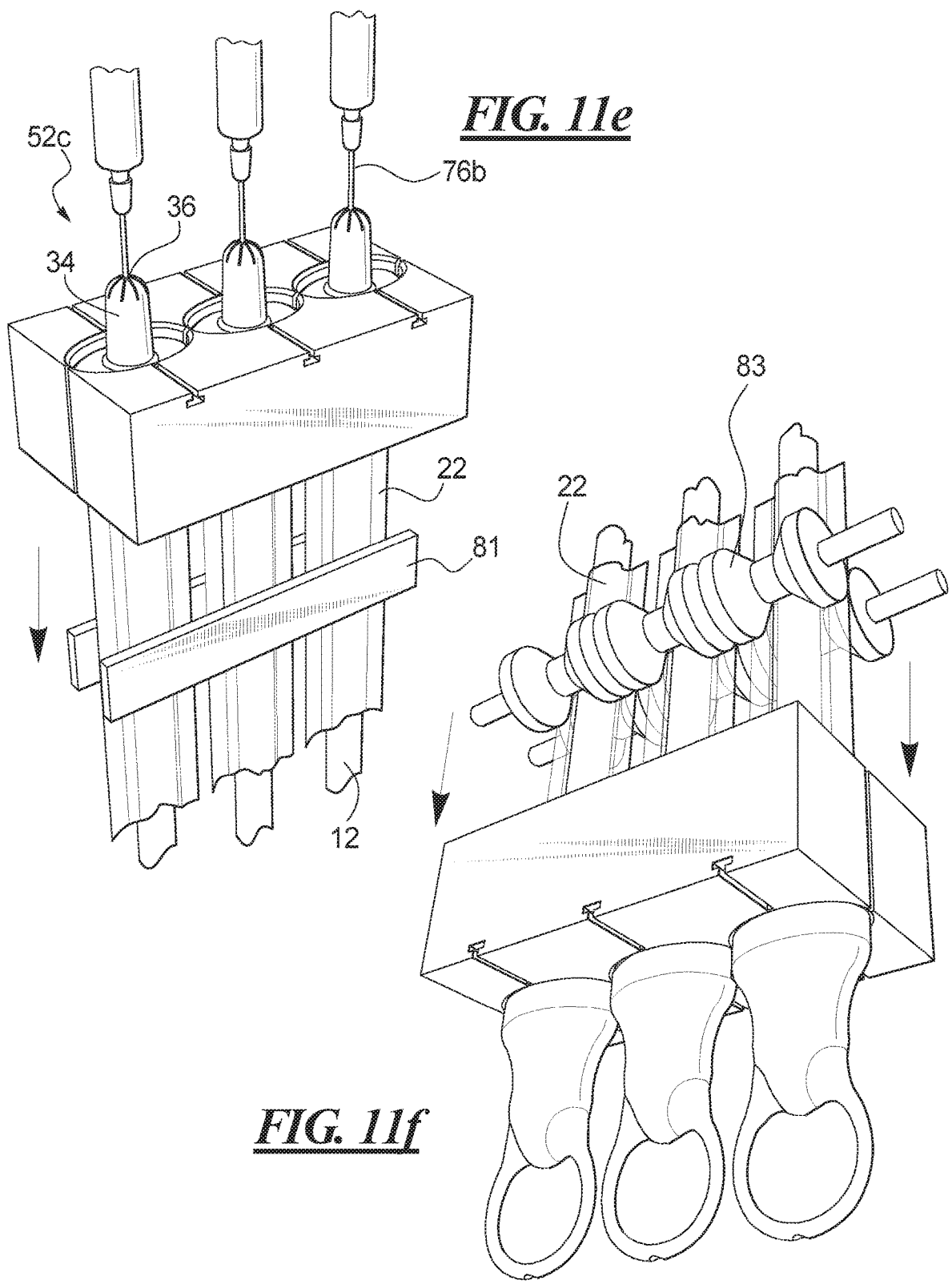

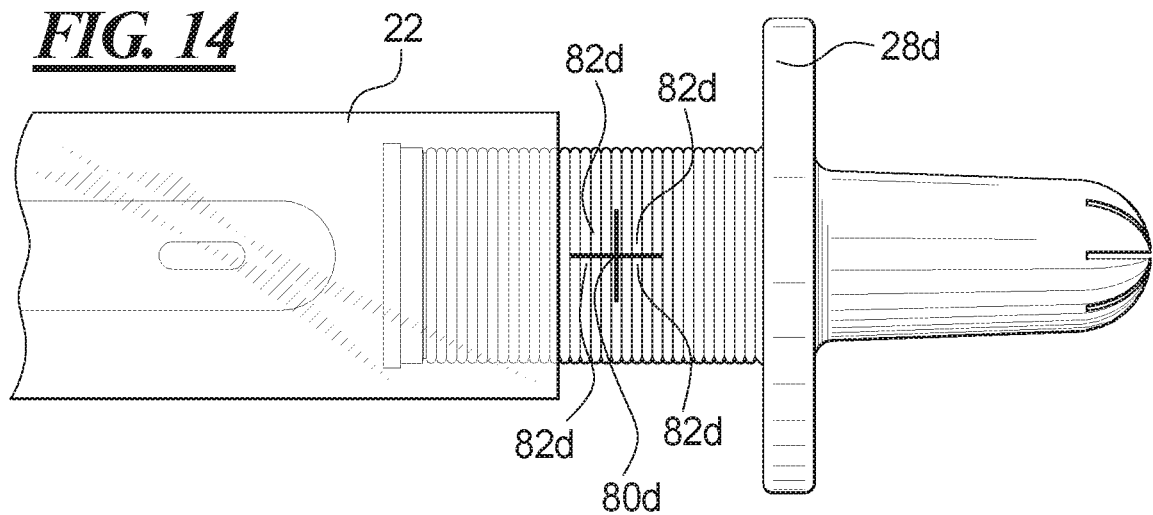
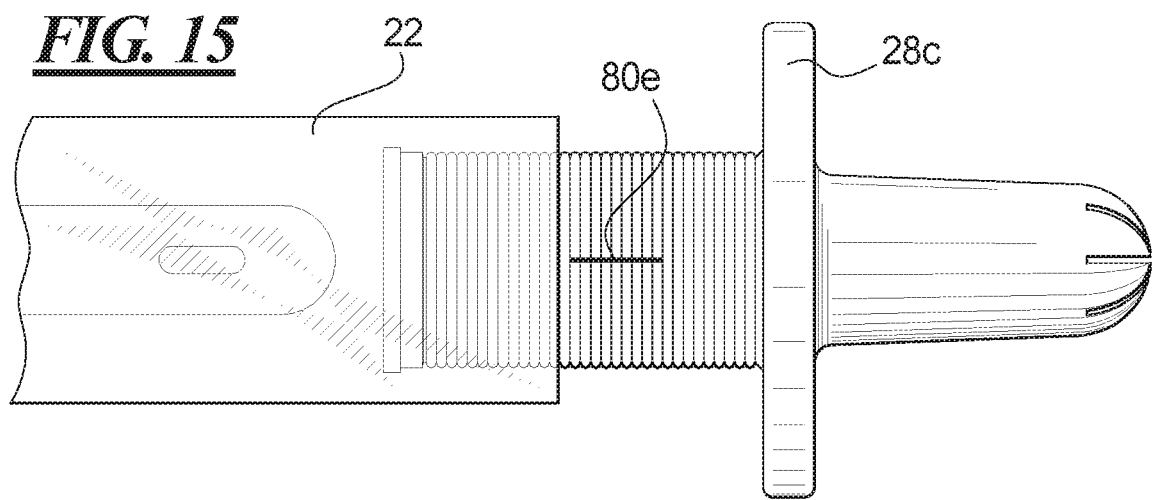
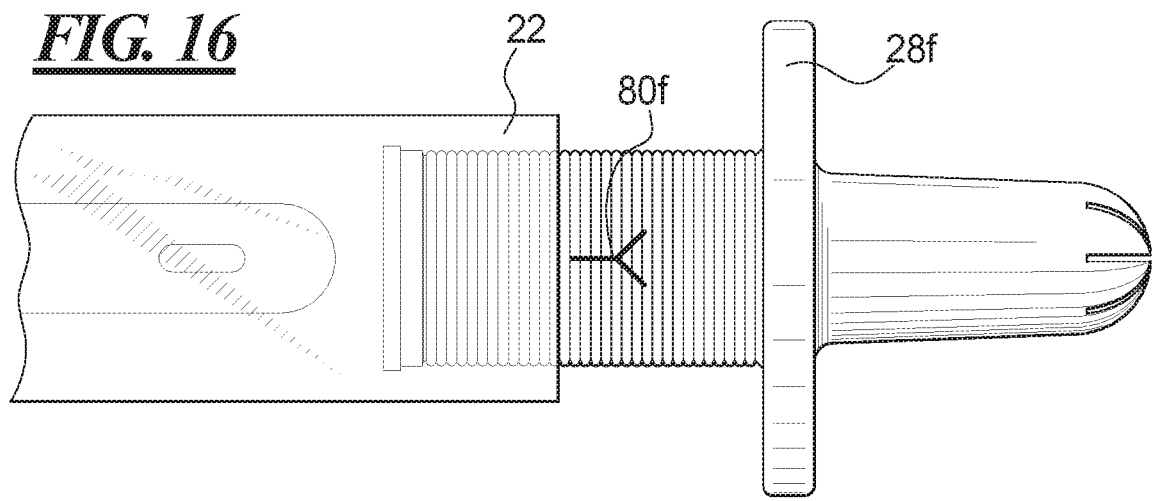

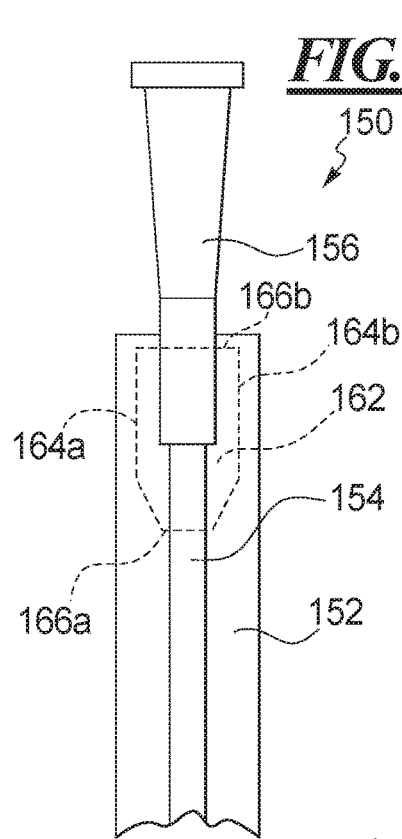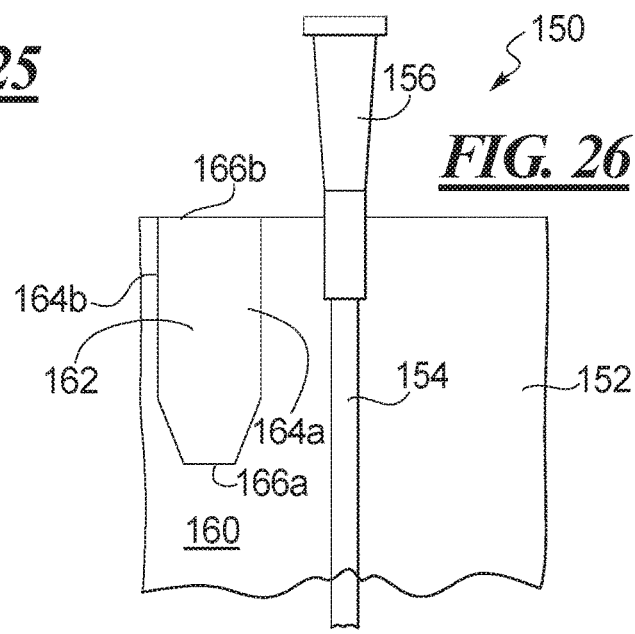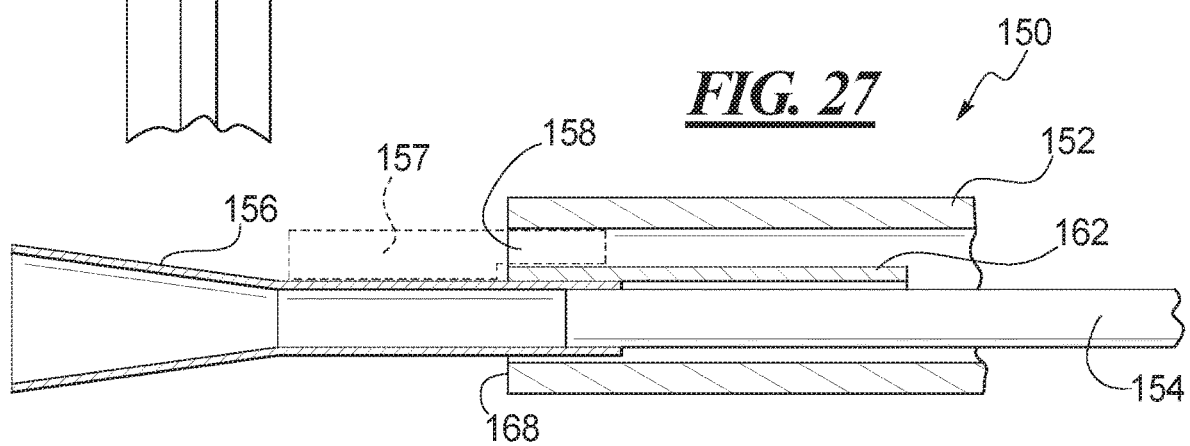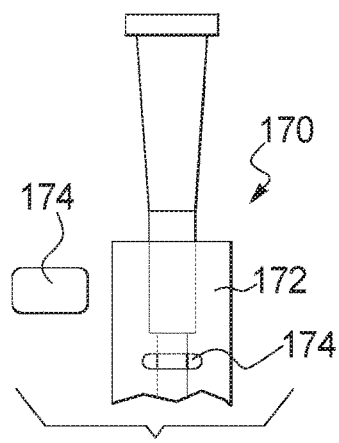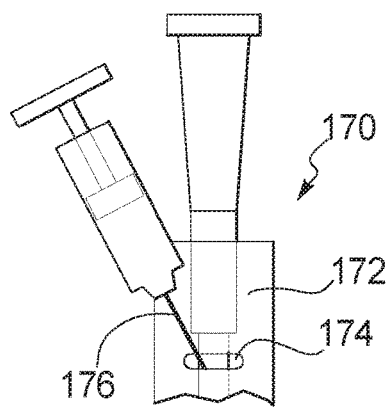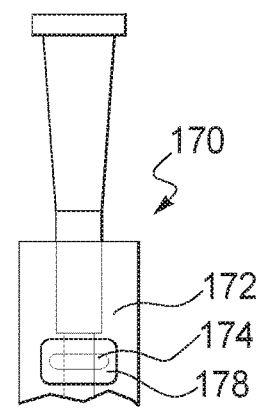

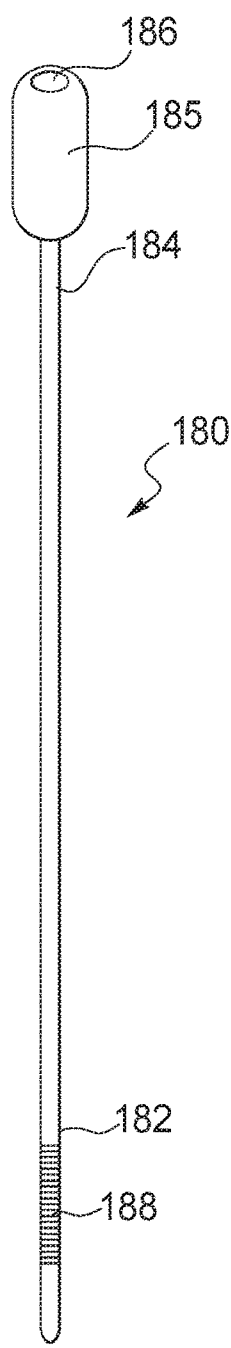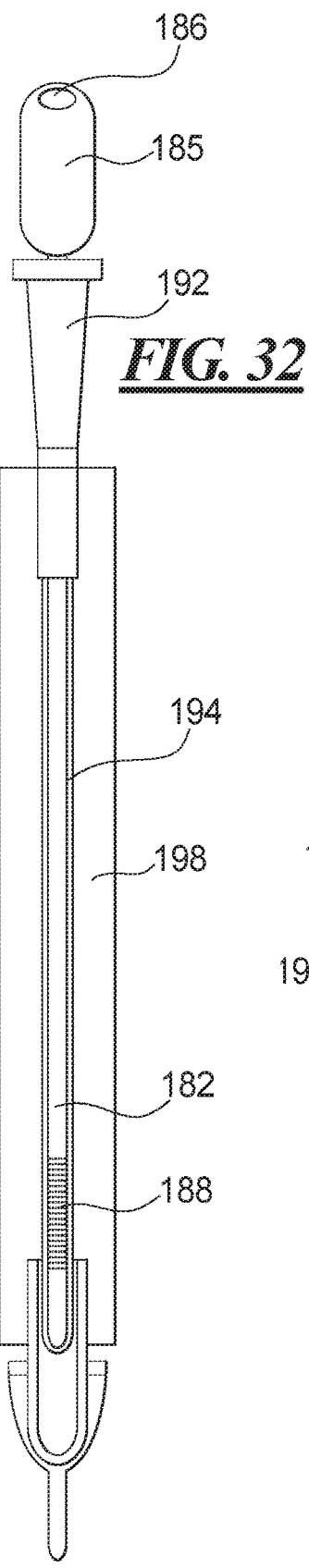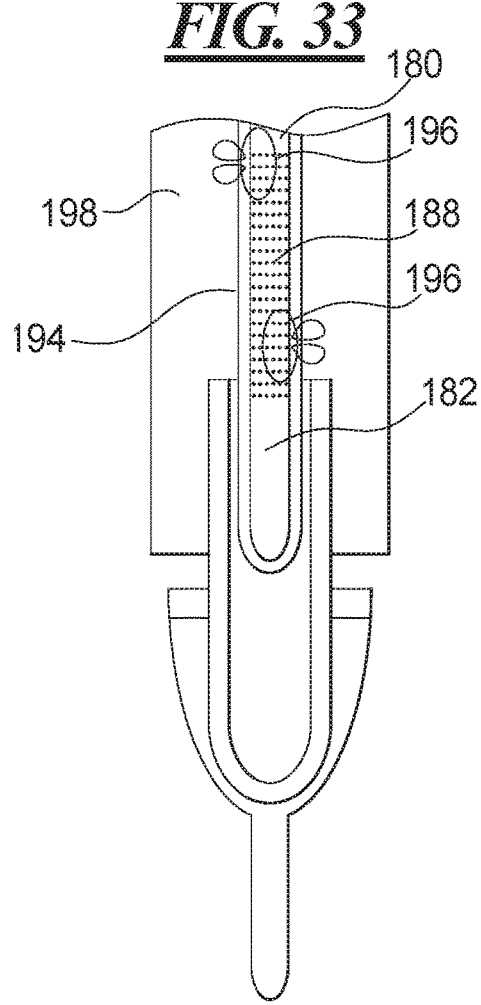

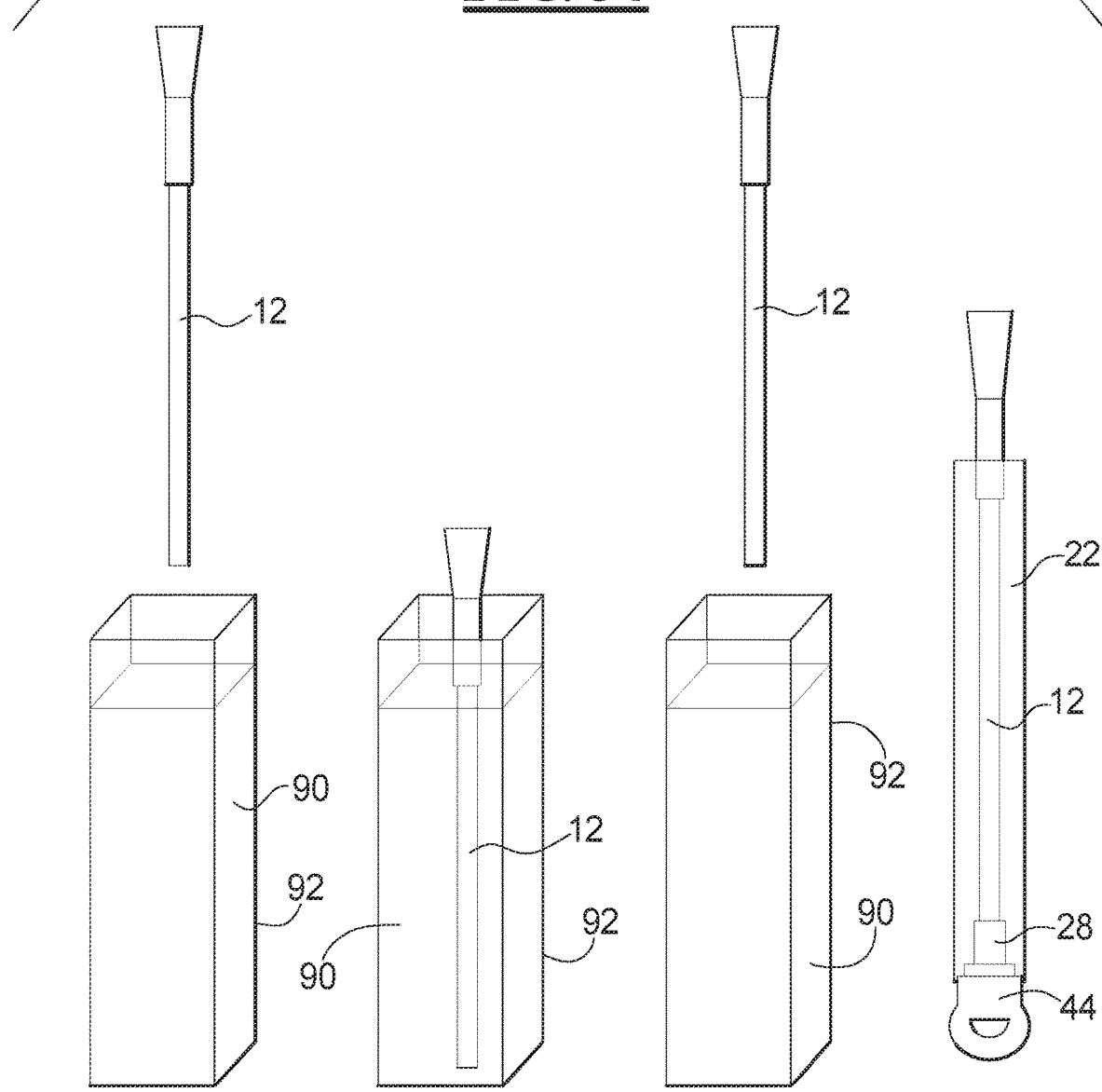

METHODS OF MAKING SLEEVED HYDROPHILIC CATHETER ASSEMBLIES

The present application is the U.S. National Stage of International Application No. PCT/US2019/032892, filed May 17, 2019, which claims the benefit and priority to U.S. Provisional Application No. 62/672,755, filed May 17, 2018, U.S. Provisional Application No. 62/699,993, filed Jul. 18, 2018, U.S. Provisional Application No. 62/739,449, filed Oct. 1, 2018, U.S. Provisional Application No. 62/770,275, filed Nov. 21, 2018, U.S. Provisional Application No. 62/821,268, filed Mar. 20, 2019, U.S. Provisional Application No. 62/821,284, filed Mar. 20, 2019, and U.S. Provisional Application No. 62/842,318, filed May 2, 2019, all of which are hereby incorporated herein by reference.

TECHNICAL FIELD

The present disclosure generally relates to methods of making sleeved hydrophilic catheter assemblies wherein the catheter assemblies include a catheter tube that has an activated or hydrated hydrophilic outer surface and a barrier sleeve surrounds the catheter tube wherein the sleeve is used to grasp the catheter for manipulation and insertion into the patient.

BACKGROUND

It is known to coat medical devices, such as urinary catheters, with a hydrophilic coating. When the hydrophilic coating is wetted or hydrated with a hydration medium it becomes extremely lubricous. The hydration medium may be, for example, liquid or vapor water or an aqueous solution. The lubriciousness of the hydrophilic coating eases introduction of the device into the body and aids in reducing pain and discomfort associated with such introduction.

In some urinary catheter products, the user directly contacts the urinary catheter with the user's fingers to remove the catheter from the package and inserts it into the urethra. In such products there may be a disadvantage in that the handling of the catheter by the user may introduce microorganisms onto the surface of the catheter which can cause infectious problems after being introduced into the body during catheter insertion. To address this issue, manufacturers have devised systems that include a protective or barrier sleeve surrounding the catheter. In this type of product, the catheter tube is located in a barrier sleeve. The sleeve may loosely fit the diameter of the catheter so that the user may grasp the catheter tube through the sleeve to manipulate the catheter, e.g., remove the catheter from its package and advance the catheter into the urethra. In some products, the distal end of the sleeve may be attached to the drainage member of the catheter and an insertion aid may be attached to or otherwise associated with the proximal end of the sleeve.

One complication of employing a sleeve over a hydrophilic catheter is how to activate or hydrate the hydrophilic surface of the catheter located within the interior cavity of the sleeve.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method of making a urinary catheter product, wherein the product includes a sleeve defining an inner cavity and a urinary catheter having a catheter tube located within the inner cavity of the sleeve, the catheter tube having an outer hydrophilic surface, an insertion aid at the distal end of the sleeve configured for passage of the catheter tube therethrough during catheterization, the method comprising delivering a hydration medium through the insertion aid and into the interior cavity of the sleeve, wherein the hydration medium contacts the outer hydrophilic surface of the catheter tube.

In another aspect, a system for delivering hydration medium into a catheter assembly. The system includes a source of hydration fluid and a nozzle in communication with the source of hydration fluid. The nozzle is configured to dock with an insertion aid of a catheter assembly and deliver hydration fluid into the catheter assembly.

In another aspect, a method of making a urinary catheter product, wherein the product includes a sleeve defining an inner cavity and a urinary catheter having a catheter tube located within the inner cavity of the sleeve, the sleeve defining at least one opening or a passageway for injecting and/or withdrawing hydration medium, the method comprising delivering a hydration medium through the insertion aid and into the interior cavity of the sleeve, wherein the hydration medium contacts the outer hydrophilic surface of the catheter tube.

In another aspect, a method of making a catheter product, wherein the product includes a sleeve defining an inner cavity and a urinary catheter having a catheter tube located within the inner cavity of the sleeve, the method comprising inserting a mandrel into a drainage member of the catheter tube and delivering a hydration fluid through the mandrel.

In yet another aspect, a method of making a urinary catheter product, wherein the product includes a sleeve defining an inner cavity and a urinary catheter having a catheter tube located within the inner cavity of the sleeve, the catheter tube having an outer hydrophilic surface, drainage member at the proximal end of the sleeve, the method comprising delivering a hydration medium drainage member and into the interior cavity of the sleeve, wherein the hydration medium contacts the outer hydrophilic surface of the catheter tube.

In another aspect, a method of making a catheter assembly that includes a catheter having a catheter tube with an outer hydrophilic surface and a sleeve defining an interior cavity, the catheter tube being located within the interior cavity of the sleeve. The method includes injecting a hydration medium into the interior cavity of the sleeve, wherein the hydration medium is in contact with the outer hydrophilic surface of the catheter tube. The sleeve having the catheter tube therein is then placed in an outer package.

In another aspect, a method of making a catheter assembly that includes a catheter having a catheter tube with an outer hydrophilic surface and a sleeve defining an interior cavity, the catheter tube being located within the interior cavity of the sleeve. The method includes applying a hydration medium to the catheter tube. The sleeve is then assembled around the catheter tube so that the catheter is located in the interior cavity of the sleeve. The sleeve having the catheter tube therein is then placed in a package.

BRIEF DESCRIPTION OF FIGURES

FIG. 1 is a perspective view of a catheter assembly in accordance with the present disclosure;

FIG. 2 is a perspective view of one embodiment of an insertion aid of the assembly of FIG. 1;

FIG. 3 is a perspective view of another embodiment of an insertion aid of the assembly of FIG. 1;

FIG. 4 is a schematic view of one embodiment of a method of making a hydrophilic sleeved catheter assembly and a hydration medium delivery device in accordance with the present disclosure;

FIG. 5 is a cross-sectional view of a nozzle engaging the insertion aid shown in FIG. 2;

FIG. 6 is a cross-sectional view of a nozzle engaging the insertion aid shown in FIG. 3;

FIGS. 7 and 8 are cross-sectional views showing another nozzle of the present disclosure;

FIG. 11a is a perspective view of an alternative to the delivery system;

FIG. 11b and 11c are perspective views of another alternative to the delivery system;

FIGS. 11d and 11e are perspective views of another alternative to the delivery system;

FIG. 11f is a perspective view of another alternative delivery system;

FIGS. 12-18 are views of insertion aids that include one or more openings or passages for injecting hydration medium into the interior cavity of the sleeve;

FIG. 25 is a plan view of another embodiment of a catheter assembly in accordance with the present disclosure;

FIG. 26 is a plan view of the catheter assembly of FIG. 25 showing the inner surface of the sleeve;

FIG. 27 is a cross-sectional view of the catheter assembly of FIG. 25;

FIGS. 28-30 are schematic views showing another embodiment of a catheter assembly in accordance with the present disclosure;

FIG. 31 is a perspective view of one embodiment of a hydration medium delivery mandrel in accordance with the present disclosure;

FIGS. 32 and 33 are partial cross-sectional view showing the hydration medium mandrel within a catheter assembly; and FIG. 34 is a schematic view of one embodiment of a method of making a hydrophilic sleeved catheter assembly in accordance with the present disclosure;

DETAILED DESCRIPTION OF THE ILLUSTRATED EMBODIMENTS

Figure 9:
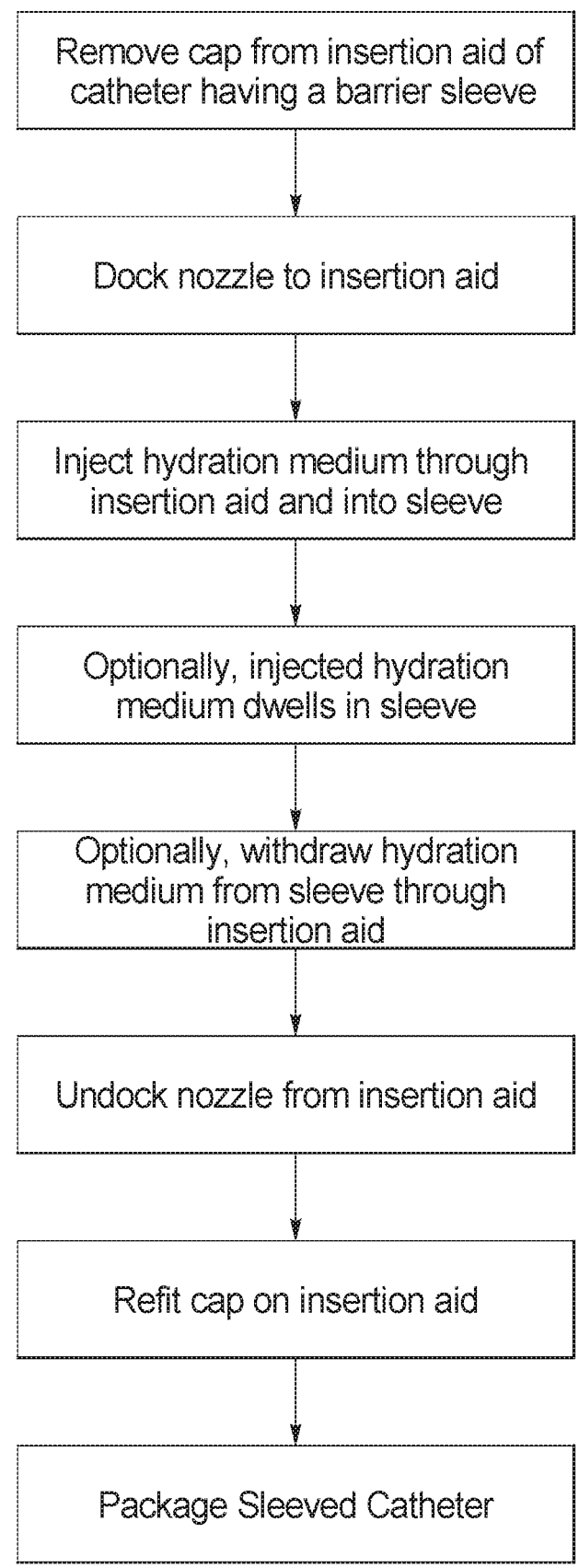
FIG. 9 is a flow chart illustrating one embodiment of a method for forming a sleeved catheter.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure is directed to methods of making a sleeved hydrophilic urinary catheter product wherein the sleeved catheter is contained in an outer package and the urinary catheter is ready-to-use right out of the outer package. That is, while in the package, the hydrophilic outer surface of the catheter tube within the interior cavity of the sleeve is in a hydrated/activated state, so that the catheter is ready-to-use right out of the package.

FIG. 1 illustrates one embodiment of a catheter assembly 10 in accordance with present disclosure. The catheter assembly 10 includes an elongated catheter tube 12 having a proximal end portion 14 and a distal end portion 16. The proximal end portion 14 of the catheter tube 12 is suitable for insertion into a lumen or a passageway of the body, such as the urethra. The proximal end portion 14 may include drainage holes or eyelets 18 for draining urine from the bladder. A drainage member 20 may be associated with the distal end portion 16 of the catheter tube 12. The catheter tube 12 includes an outer hydrophilic surface that becomes lubricious when hydrated or activated. The outer surface may be, for example, any suitable hydrophilic coating.

The catheter assembly 10 also includes a sleeve 22, which may be a protective or barrier sleeve that has a proximal end portion 24 and a distal end portion 26. The sleeve 22 surrounds at least a portion of the catheter tube 12 to separate and enclose the portion of the catheter tube 12 from the outside environment. In other words, the protective sleeve 22 defines an interior cavity in which the catheter tube 12 may be located. In one embodiment, the sleeve 22 extends over the length of the catheter tube 12. Optionally, an insertion aid 28 may be located at the proximal end portion 24 of the sleeve 22. When an insertion aid 28 is present, the proximal end portion 24 of the sleeve 22 may be attached to a barrel or stem 30 of the insertion aid 28, by for example, welding or adhesive. The distal end portion 26 of the sleeve 22 may be attached to the drainage member 20 or the distal end of the catheter tube 12. An insertion aid may be used with any of the catheter assemblies disclosed herein.

The sleeve 22 and any of the other sleeves disclosed herein may be made of a flexible material which may be vapor permeable or vapor impermeable, depending on the desired use and packaging. The material of the sleeve 22 may also be liquid impermeable. The sleeve 22 may be formed of any of a variety of thin, flexible polymeric film materials, such as polyethylene, plasticized PVC, or polypropylene, but elastomeric film materials such as polyurethane, and particularly elastomeric hydrogel materials, may be particularly suitable. The thickness of the film from which the sleeve 22 is formed may vary considerably depending on factors such as stretchability and flexibility of the material selected but, in general, the thickness may fall within the range of about 10 to 150 microns, preferably about 13 to 50 microns.

Referring to FIGS. 1, 2 and 3, these figures illustrate exemplary embodiments of the insertion aids. In FIGS. 1 and 2, the insertion aid 28 includes a proximal end portion 32 that defines an introducer tip 34. The introducer tip 34 has a proximal end aperture or opening 36 defined by one or more slits between one or more flexible petals 38. The petals 38 may move, bend and/or resiliently deform from the generally closed aperture configuration shown in FIGS. 1 and 2 to an open aperture configuration (not shown) to allow for advancement of the catheter tube 12 therethrough. The distal end portion of the insertion aid 28 includes a cylindrical or barrel portion 30 that has an opening 40 for receiving the catheter tube 12. The insertion aid 28 may also include an intermediate flange 42 that may contact the user about the urethra opening and act as a stop to limit the insertion of the introducer tip 34.

Turning to FIG. 3, in this embodiment the insertion aid 28*a* is a port 29*a* that includes a flange 42*a* surrounding an aperture or opening 34*a*. The catheter tube 12 advances through opening 34*a* for insertion into the urethra. The distal end portion of the port 29*a* includes a cylindrical or barrel portion 30*a* that has an opening 40*a* for receiving the catheter tube 12.

Turning back to FIG. 1, the insertion aid 28, optionally, may be covered by a removable protective cap 44. The removable protective cap 44 covers the insertion aid 28 and may protect the insertion aid 28 from contacting surfaces and objects prior to use.

To use the catheter assembly 10, the user opens and removes the catheter assembly 10 from an outer package (not shown). For example, the user opens the package and grasps the catheter tube 12 through the protective sleeve 22 to handle and manipulate the catheter assembly 10. The user removes protective cap 44, if one is present. If the catheter assembly 10 includes the insertion aid 28 shown in FIG. 2, then the user inserts the introducer tip 34 into the urethra. If the catheter assembly 10 includes the insertion aid 28*a* shown in FIG. 3, then the user aligns the opening 34*a* of the port 29*a* with the urethral opening. The user then grasps the catheter tube 12 through the sleeve 22 and advances the catheter tube 12 through the insertion aid 28/28*a* and into and through the urethra until the eyelets enter the bladder. If the catheter assembly 10 does not includes an insertion aid, then the user grasps the catheter tube 12 through the sleeve 22 and advances the tip of the catheter tube 12 out of the open end of the sleeve 22 and into the urethra. When the eyelets enter the bladder, urine flows through the eyelets and catheter tube 12 to drain the bladder.

In one method of making a sleeved hydrophilic catheter wherein the hydrophilic surface is in an activated or hydrated state, such as those described above, the method includes injecting or delivering a hydration medium into the interior cavity of the sleeve of the catheter assembly. While in the sleeve, the hydration medium contacts the hydrophilic surface of the catheter to at least partially hydrate or activate the hydrophilic surface, and in one embodiment, fully hydrate the hydrophilic surface. Optionally, the hydration medium dwells within the sleeve for a selected time period, which may be sufficient to partially or fully hydrate/activate the hydrophilic surface. Also optionally, an amount of hydration medium may be selectively withdrawn or extracted from the interior cavity of the sleeve. For example, some or all of the loose hydration medium may be withdrawn from the sleeve. The hydration medium within the hydrophilic surface will substantially remain within the hydrophilic coating and within the sleeve.

The hydration medium may be a liquid, foam or a gel. For example, the hydration may be liquid water or an aqueous solution or any other suitable liquid hydration medium. In one embodiment, the hydration medium may be an aqueous solution that includes water, glycerol and, optionally, other additives.

Optionally, the hydration medium may be a hydration foam that includes a liquid containing a mass of gas bubbles on or in the liquid. In one embodiment, the hydration foam medium includes, among other components, a liquid, a surfactant and gas. The liquid may be water or an aqueous solution. The surfactant may be any suitable foaming agent or surface tension reducing agent, such as sodium methyl cocoyl taurate or the like. The gas may be any suitable gas, such as ambient air, carbon dioxide, nitrogen, etc. The gas may be homogenized with the liquid to form a foam. When the hydration medium is a hydration foam, the hydration medium may be foamed and then delivered into the sleeve. Alternatively, the hydration medium may be foamed at the same time as it is delivered into the sleeve, or may be foamed after it is delivered into the sleeve.

In another embodiment, the hydration medium may be a water based gel. The gel based hydration medium may have a dual function, firstly hydrates hydrophilic coating and secondly protects retention of water. In one embodiment, the gel may be one that liquefies or becomes less viscous when exposed to radiation and may supplement hydration and lubriciousness of hydrophilic coating. For example, the gel may be a gellan gum based gel that is injected into the sleeve as a gel and then liquefies, breakdowns or becomes less viscous when the catheter assembly is exposed to sterilizing radiation, such as e-beam or gamma radiation. In one embodiment the gel may be a gel that includes 1.5 wt %-2 wt % of gellan gum, 1 wt % glycerol and 97 wt %-97.5 wt % of water.

As will be discussed in more detail below, the hydration medium (liquid or gel) may have an elevated temperature during injection into the interior cavity of the sleeve. For example, the hydration medium may be at a temperature between 15° C.-70° C. In another embodiment, the hydration medium may be at a temperature between 40° C.-70° C. during injection. Any hydration medium not withdrawn from the sleeve and remaining in the sleeve after the withdrawal step may be allowed to cool to ambient temperatures. Injecting the hydration medium at an elevated temperature may assist in injecting and/or withdrawing the hydration medium. Additionally, injecting a hydration medium at an elevated temperature may lessen the time it takes for the hydration medium to hydrate/activate the hydrophilic surface of the catheter.

When the hydration medium is a gel, the gel may be injected into the sleeve as a hot gel solution at an elevated temperature, as discussed above. The hot gel solution may partially or substantially hydrate the hydrophilic coating of the catheter tube. Optionally, a selected amount of the hot gel solution may be withdrawn. Alternatively, the method may not include a withdrawal step. The gel in the sleeve or remaining in the sleeve after a withdrawal step may cool to ambient temperatures (e.g., about 23° C. or below). When the gel cools, it may form a thin gel coating, such as a hydrogel coating, at least partially covering, and preferably substantially covering, the partially or substantially hydrated hydrophilic surface of the catheter tube. Additionally, there may be surplus deposits of gel located within the sleeve. Such gel deposits may be gel that is in the sleeve but not covering the catheter. Depending on the gel used, the gel may not hydrate the hydrophilic surface of the catheter while in the gel state, at least partially hydrate the hydrophilic surface of the catheter while in the gel state, or fully hydrate the hydrophilic surface of the catheter while in the gel state.

Furthermore, the gel may be a gel that liquefies or becomes less viscous when the catheter assembly is exposed to sterilizing radiation. For example, after the gel injection step and optional withdrawal step, the gel may be covering the hydrophilic surface of the catheter and/or may otherwise be located in the sleeve. The catheter assembly is then placed in a package. The package may then be exposed to sterilizing radiation wherein the gel liquefies or becomes less viscous.

Turning now to FIG. 4, this figure provides a schematic representation of a fill method that includes an injection system 52 for delivering hydration medium into the sleeve 22. Optionally, the system 52 may also have the capabilities of withdrawing hydration medium from the sleeve. The catheter assembly 10 may be docked or otherwise operatively connected to a hydration medium injection system or machine 52. The hydration medium injection and system 52 may include a source of hydration medium 54, which could be a reservoir or tank containing an amount of hydration medium 56. The system may include a conduit 58, one end 60 of which is connected to the source of hydration medium 54, and the end 62 of which is configured to be connected or docked to the catheter assembly 10 so that hydration medium 54 can be injected or delivered into and, optionally withdrawn from, the interior cavity of the sleeve 22. For example, the end 62 of the conduit 58 may include a nozzle 64 configured to be releasably connectable/docked to the sleeve 22 or the insertion aid 28, if one is present. The system also includes a pump or metering valves or other element 66 for moving/pumping hydration medium 56 so as to inject hydration medium into the sleeve 22. The pump or other element 66 may also move/pump hydration medium 56 so as to withdraw or extract hydration medium 56 from the sleeve 22 and back into hydration source 54. The injection and withdrawal pumps/metering valves/elements may be the same or different elements. For example, the system may include a reversible pump that injects and withdraws hydration medium, or the system may include one pump for injecting medium and another pump for withdrawing medium.

As discussed above, the method of forming the sleeved activated hydrophilic catheter may include, injecting a hydration medium into the interior cavity of the sleeve, wherein the hydration medium comes into contact with the outer hydrophilic surface of the catheter tube. Optionally, allowing the hydration medium to dwell within the sleeve for a desired dwell time. Then, withdrawing at least some of the hydration medium from the interior cavity of the sleeve and placing the sleeve having the catheter tube therein in an outer package.

Referring to FIGS. 4 and 9, there is shown and described one exemplary embodiment of forming the sleeved hydrophilic catheter shown in FIG. 1. If a protective cap 44 is present, the method includes removing protective cap 44 from the insertion aid 28. The nozzle 64 of the injection system is then docked or connected to the insertion aid 28. If the insertion aid 28 includes an introducer tip 34, the nozzle 64 may be dock to the catheter assembly 10 by inserting the introducer tip 34 into the nozzle 64, as shown in FIG. 5. The inner diameter of the nozzle 64 may have a size that generally corresponds to the outer diameter of the introducer tip 34. As shown in FIGS. 7 and 8, the nozzle 64a may be a universal nozzle that may be configured to receive different sized introducer tips. For example, the inner surface of the nozzle 64a may be stepped or include multiple steps 68a or may have a generally cone shaped configuration for engaging and docking with different sized introducer tips 34a, e.g., introducer tips having different sized diameters.

Referring to FIG. 6, when the insertion aid 28a is a port 29a, the nozzle 64b may also be configured to dock to the port 29a.

Turning back to FIGS. 4 and 9, after the nozzle 64 is dock, hydration medium 56 is injected from the nozzle 64 through the insertion aid 28 and into the sleeve 22 wherein the hydration medium contacts the hydrophilic surface of the catheter tube 12. As mentioned above, the hydration medium may be injected at an elevated temperature. Furthermore, when an insertion aid 28 is present, the hydration medium 56 may be injected through the aperture 36 defined by slits and petals 38 (FIG. 2). The petals 38 may resiliently deform to allow passage of the hydration medium 56 and/or the slits may have dimensions that allow for passage of hydration medium 56.

Optionally, the injected hydration medium 56 dwells in the sleeve 22 for a desired amount of time. For example, the dwell time may be a time that is sufficient for the hydration medium 56 to fully activate or fully hydrate the hydrophilic outer surface of the catheter tube 12. In some embodiments, it may be desirable for the dwell time to be sufficient to partially hydrate or partially activate the hydrophilic outer surface of the catheter tube. Optionally, at least some of the hydration medium 56 is then withdrawn from the sleeve 22 through the insertion aid 28. In one embodiment, substantially all of the loose hydration medium 56 is withdrawn from the sleeve 22. That is, the hydration medium 56 that is loose within the sleeve 22 is withdrawn while the hydration medium that has been absorbed by the hydrophilic surface of the catheter tube 12 remains within the hydrophilic surface and the sleeve. In other embodiments, some of the loose hydration medium 56 is withdrawn and some is left in the sleeve 22.

After the hydration medium 56 has been withdrawn, the nozzle 64 is undocked and the protective cap 44 is placed on or refitted onto the insertion aid 28. The catheter assembly 10 is then placed within an outer package (not shown) and the package is sealed. The outer package may then be submitted to sterilizing by e-beam or gamma radiation.

In one embodiment, the outer package may be made of a gas impermeable and liquid impermeable material, such as a polymer and aluminum laminate. Furthermore, the package may be of the type that has a vapor atmosphere or 100% relative humidity within the seal package. For example, the package may include therein a water compartment that is at least partial defined by a vapor permeable, liquid impermeable material. The water within the compartment may produce a water vapor that permeates through the vapor permeable, liquid impermeable material to create and/or maintain a hydration environment within the package. Additionally, when the catheter assembly is placed in a package having a vapor atmosphere, the sleeve may be vapor permeable to allow vapor to come into contact with the partially or substantially hydrated hydrophilic surface of the catheter tube. This may assist in maintaining the hydrophilic surface in an activated or hydrated state during storage and distribution. Alternatively, when the sleeve is made from a liquid and gas impermeable material and the interior cavity of the sleeve is sealed off, the outer package may be made from a gas permeable material.

Figure 10:
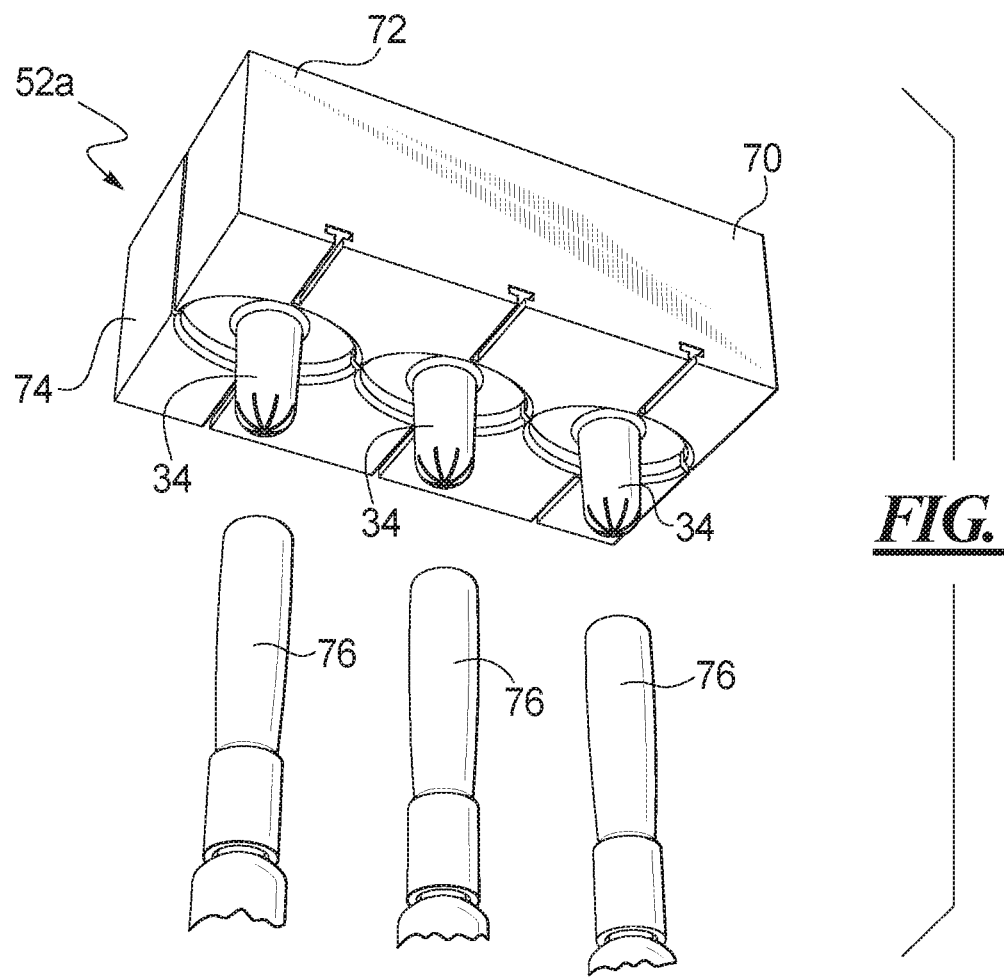
FIGS. 10 and 11 are perspective views of a system for delivering and/or withdrawing hydration medium from sleeved catheters.
Figure 11:
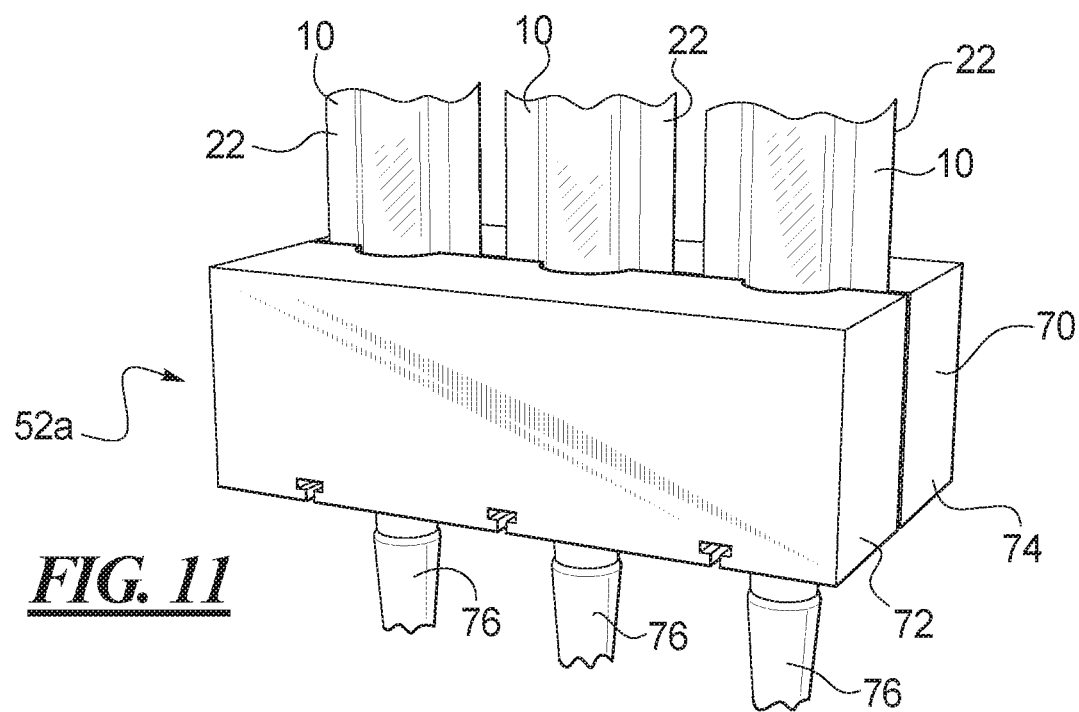

FIGS. 10 and 11 illustrate a portion of an injection system 52a which may be employed to inject hydration medium into and, optionally withdraw hydration medium from, the interior cavity of the sleeve 22. The system 52a may include a holder 70 configured to accept and hold a plurality of catheter assemblies 10. In the illustrated embodiment, the holder 70 includes a plurality of cavities for accepting and holding the catheter assemblies 10. The holder 70 may include a body having separable front and rear body portions 72 and 74, which separate to receive the catheter assemblies 10 into the respective cavities. The front and rear body portions 72 and 74 come together to orientate and hold the catheter assemblies 10 in place. After the catheter assemblies 10 are located in the holder 70, the nozzles 76 may be docked or connected to the catheter assemblies 10. In the illustrated embodiment, the nozzles 76 connect or dock to the introducer tips 34 of the catheter assemblies 10. The system 52*a* then injects hydration medium into the sleeve 22 and, optionally withdraws hydration medium from the sleeve, similar to that discussed above.

FIG. 11*a* illustrates alternative features of the system 52*a*. The system 52*a* may have compression members 71 that compress the introducer tips 34 of the insertion aids to place the apertures 36 of the insertion aids into the open configuration prior to or after the nozzle 76 (FIG. 11) is attached. In the illustrated embodiment, the compression members 71 include a body 75 and a stem 77. The stems 77 are located and slide in tracks 79 of the body portions 72 and 74. In the illustrate embodiment, the track may be T-shaped and the stems 77 may include a corresponding T-shape. Opposed pairs of compression members 71 are positioned on either side of the introducer tip 34 and the opposed compression members 71 move toward each other to compress the introducer tip 34 and move the apertures 36 into the open configuration.

FIG. 11*b* and 11*c* illustrate an alternative system 52*b*. The system 52*b* includes support members 71*b* located on at least one of the front and rear bodies 72 and 74 of the holder 70. The support members 71*b* support the introducer tips 34 during delivery of the hydration medium. In the illustrate embodiment, the support members 71*b* engage the introducer tips 34 when the holder is moved to the closed configuration. A nozzle or needle 76*b* may then engage the introducer tips 34 to deliver the hydration medium.

FIGS. 11*d* and 11 *e* illustrate another alternative system 52*c*. The system 52*c* includes a clamp 81 that clamps the catheter tubes 12 through the sleeves 22 and moves the catheter tubes 12 proximally and out of the introducer tips 34. The delivery members, such as needles or nozzles 76*b*, dock with the distal end of the catheter tubes 12. The camp 81 is then moved proximally to move the catheter tubes 12 and the needles 76*b* into the aperture 36 of the introducer tips 34, and the hydration medium may be delivered through the tips 34 and in to the sleeve 22.

FIG. 11*f* illustrates another alternative feature of the delivery systems. The delivery system may include disbursement members 83 that disburse the hydration fluid within the sleeve 22. In the illustrated embodiment, the disbursement members 83 include opposed rollers that contact the sleeve 22 and roll along the sleeve 22 to disburse the hydration medium therein.

FIGS. 12-20 illustrate exemplary embodiments of insertion aids and drainage members that have one or more openings or passageways therein for injecting and/or withdrawing hydration medium from the interior cavity of the sleeve 22. The insertion aids and drainage members may include an opening(s) or a passageway(s) that communicates with the interior cavity of the sleeve 22. The opening(s) or passageway(s) may be used to inject and/or withdraw hydration medium from the interior cavity of the sleeve. For example, the openings and passageways may be configured to receive a device for injecting and withdrawing hydration medium, such as a nozzle or a needle. Additionally, any of the openings or passageways disclosed herein that are in communication with the interior cavity of the sleeve, whether they are in the insertion aid, drainage member or sleeve, may also serve as a vent that vents fluid from the sleeve when the sleeve is collapsed during use.

Figure 12:
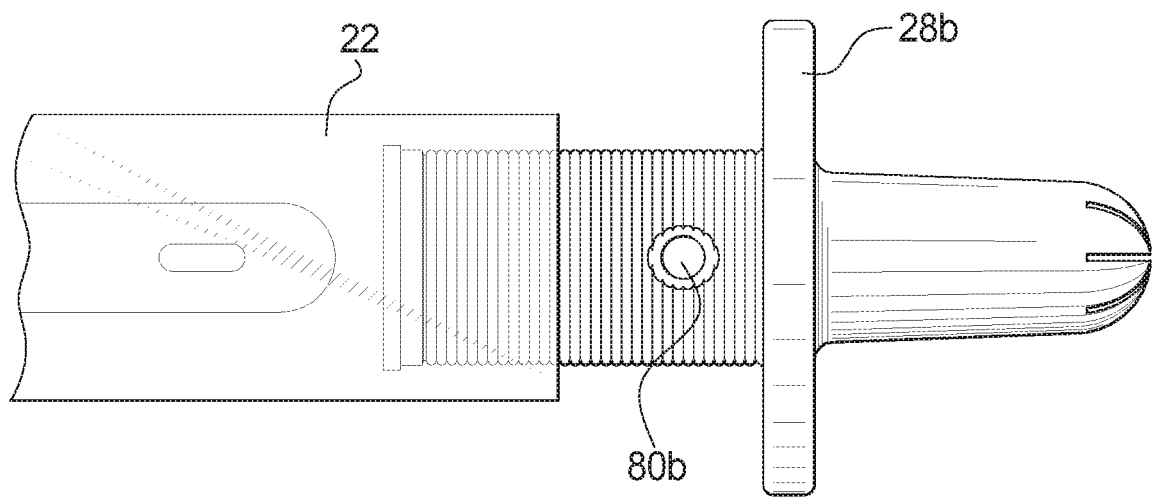
Figure 13:
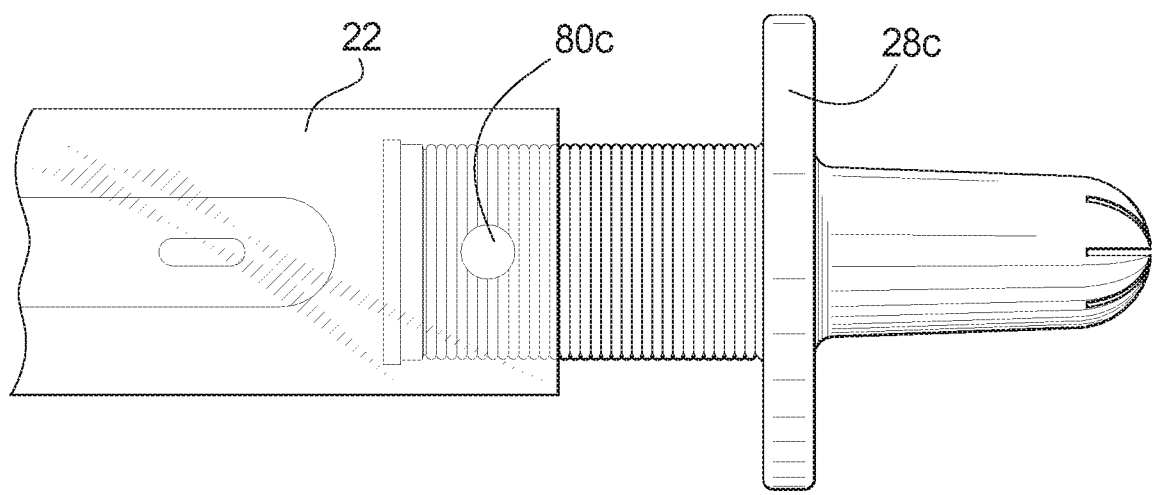
Figure 17:
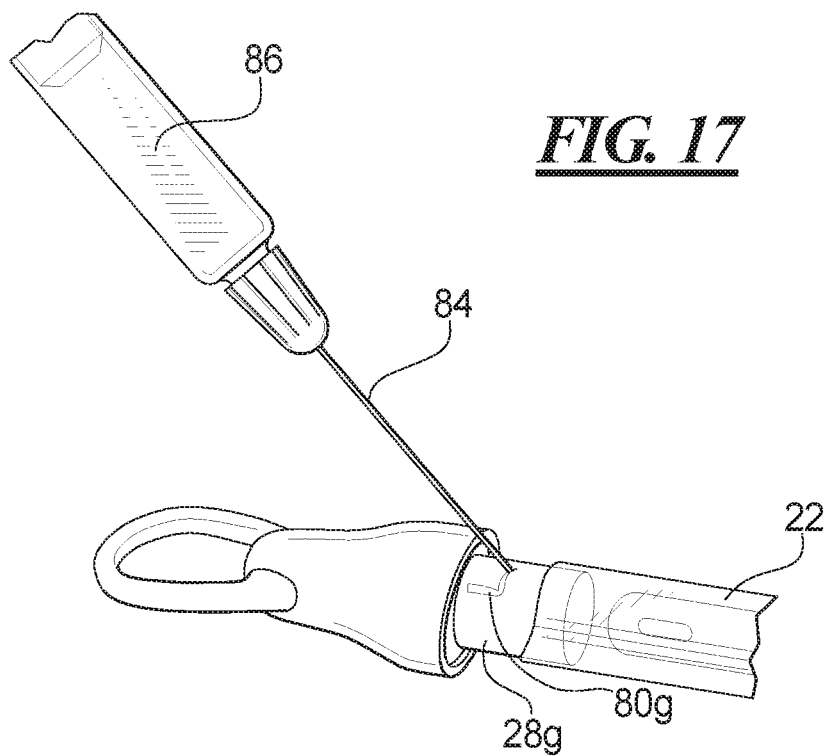
Figure 18:
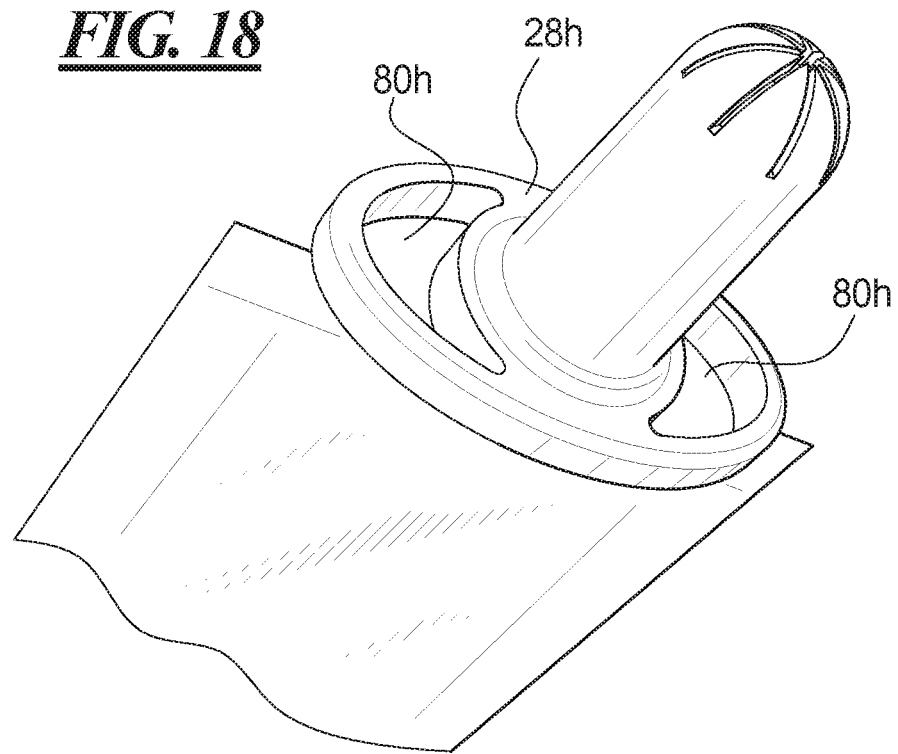

FIGS. 12-18 illustrate exemplary embodiments of insertion aids that have a structure similar to that of insertion aid 28 described above. The insertion aids shown in these figures also include an opening for injecting and withdrawing a hydration medium. Turning first to FIG. 12, in this embodiment, the insertion aid 28*b* includes an opening 80*b* in the barrel portion for injecting hydration medium into and withdrawing hydration medium from the interior cavity of the sleeve 22. In FIG. 13, the insertion aid 28*c* includes an opening 80*c* in the barrel portion for injection and/or withdrawal of hydration medium wherein the opening 80*c* is covered by a portion of the sleeve 22. In this embodiment, a needle or nozzle may penetrate the portion of the sleeve to access the opening 80*c*. In FIG. 14, the insertion aid 28*d* includes petals 82*d* in the barrel portion that form a cross-shaped deformable slit 80*d*. In FIG. 15, the insertion aid 28*e* includes a deformable slit 80*e* in the barrel portion, and in FIG. 16, the insertion aid 28*f* includes a Y-shaped slit in the barrel portion. In each of these embodiments, a nozzle may be pressed against the slits 80*d*, 80*e* and 80*f* to open the slits or a needle may penetrate the slits to inject and/or withdraw hydration medium. Additionally, similar to FIG. 13, a portion of the sleeve 22 may cover the slits 80*d*, 80*e* and 80*f*, wherein the portion of the sleeve 22 must be penetrated to access the slit. FIG. 17 illustrates another embodiment wherein the insertion aid 28*g* includes a U-shaped slit 80*g* that is accessible by a needle or nozzle 84 to inject a hydration medium 86, and optionally withdraw the hydration medium. In FIG. 18, the insertion aid 28*h* includes a plurality of axial passageways 80*h* for injecting and/or withdrawing hydration medium.

Figure 19:
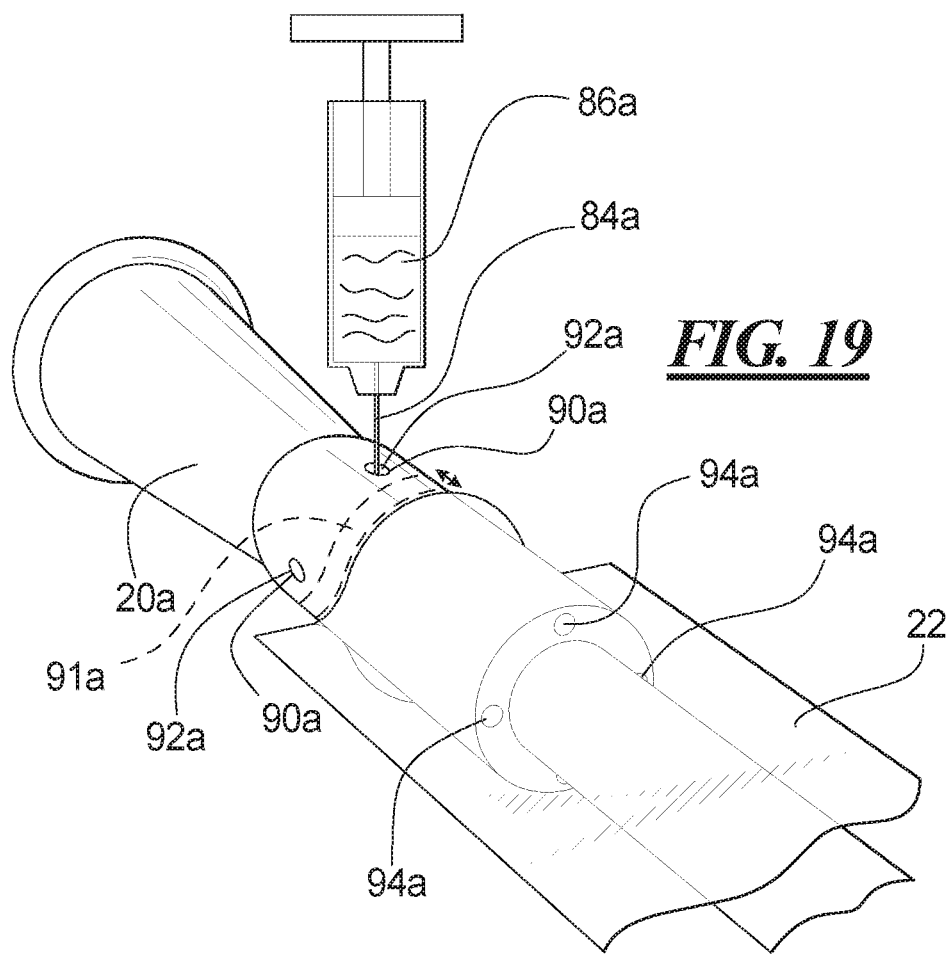
FIGS. 19 and 20 are views of drainage members that includes one or more openings or passages for injecting hydration medium into the interior cavity of the sleeve.
Figure 20:
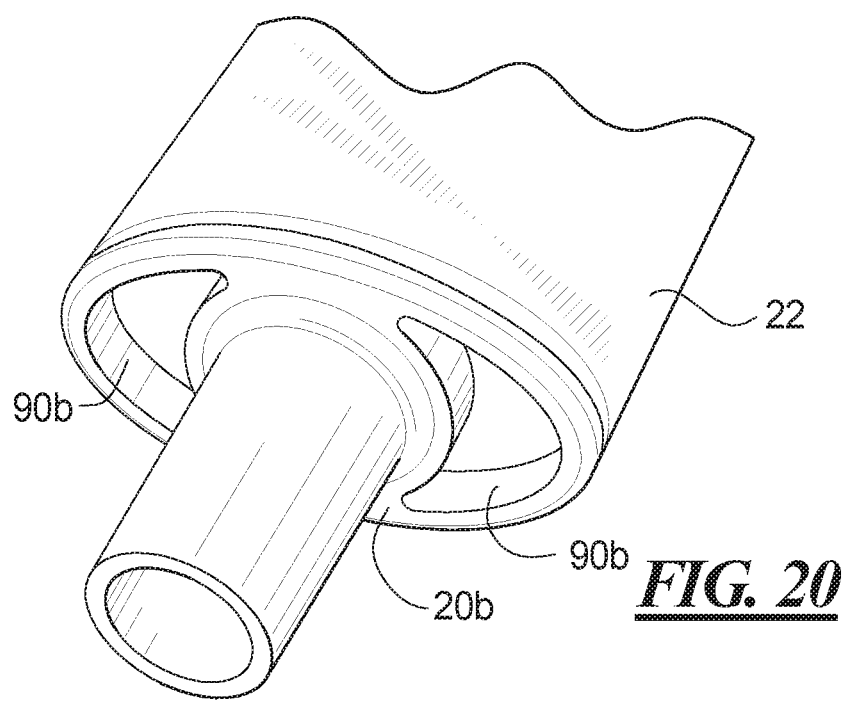

FIGS. 19 and 20 illustrate drainage members 20*a* and 20*b* that include one or more passageways that are configured for injecting hydration medium into and/or withdrawing hydration medium from the interior cavity of the sleeve 22. Turning first to FIG. 19, the drainage member 20*a* includes passageways 90*a* having an opening 92*a* external of the sleeve 22 and another opening 94*a* within the interior cavity of the sleeve 22. The external opening 92*a* is configured to receive a device, such as a nozzle or needle 84*a*, for injecting hydration medium 86*a* into and/or withdrawing hydration medium 86*a* from the sleeve 22. Optionally, the passageways 90*a* may be sealed or closed after the delivery of the hydration medium. For example, caps or plugs could be placed in the passageways 90*a*. In one embodiment, a slideable sealing ring 91*a* could be associated with the drainage member 20*a*. After the hydration medium has been delivered, the ring 91*a* can be slide over the passageways 9*ab* to close or seal them. Referring to FIG. 20, the drainage member 20*b* includes one or more axial passageways 90*b* for injecting hydration medium into and/or withdrawing hydration medium from the sleeve 22.

Another embodiment is that the nozzle may include an atomizer which converts hydration medium into small droplets which can be sprayed onto hydrophilic coating surface to induce hydration in sleeved cavity.

Another embodiment is that the hydration fluid is delivered as steam through the nozzle in sleeved cavity and onto hydrophilic coating surface to induce hydration. In another embodiment, the hydration fluid is delivered as a foam, for example, a foaming agent such as air or nitrogen could be added to the hydration fluid.

Figure 21:
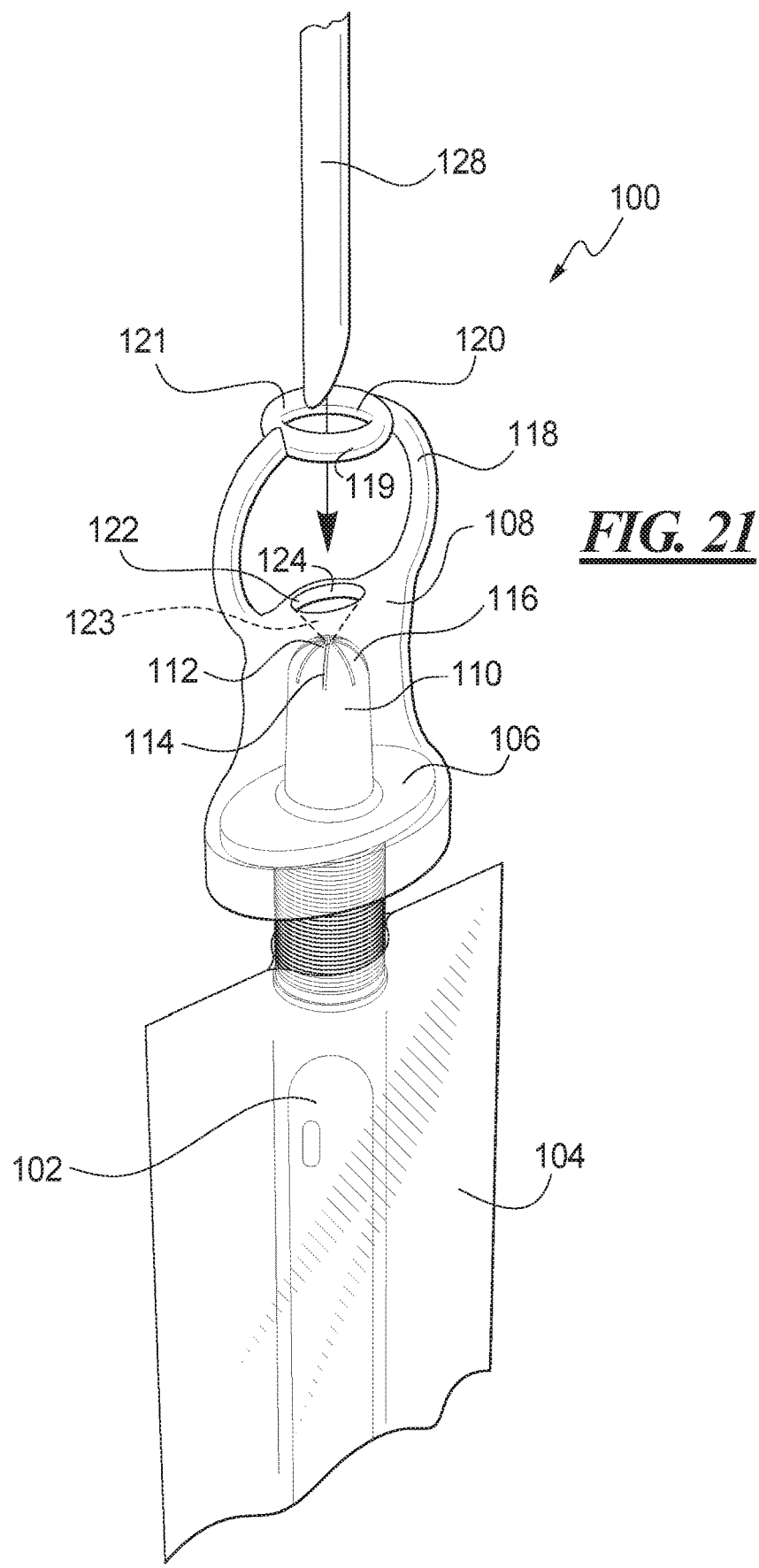
FIG. 21 is a perspective view of one embodiment of a catheter assembly in accordance with the present disclosure.

FIG. 21 illustrates another embodiment of a catheter assembly 100. The catheter assembly 100 includes catheter 102, a sleeve 104, an insertion aid 106 and a removal protective cap 108. In the illustrated embodiment, the insertion aid 106 includes an insertion tip 110 wherein the tip includes a proximal end opening 112 defined be slits 114 and petals 116. The insertion aid 106 may also be any of the insertion aids disclosed herein or any other suitable insertion aid.

The protective cap 108, optionally, includes a ring 118 at the proximal end thereof wherein the ring 118 may be sized and configured to be grasped by a user. For example, a user may grasp ring 118 or place a finger in the ring 118 to remove it from the catheter assembly 110. When a ring 118 is present, a portion 119 of the band of the ring 118 may include an opening 120 therethrough. The opening 120 in the band may be defined by a rim 121 in the portion 119. Additionally, the body of the cap 108 may include a proximal end opening 122 which may be aligned with the opening 112 of the insertion aid 106. Furthermore, the opening 120 in the portion 119 of the band of ring 118 may be aligned with the opening 122 of the cap 108. In the illustrated embodiment opening 122 of the cap 108 is defined by a rim 124. In other embodiments, the opening 122 may be defined by one or more slits (not shown) and/or petals, or it may be an opening that can be opened and closed. For example, the opening may be opened and closed by flexible material or the opening may be covered or plugged.

Optionally, the cap 108 may include a funnel member 123 that extends from opening 122 and into the opening 112 of the insertion aid 106. The delivery device 128 may be inserted through the funnel member 123, or the hydration fluid may be delivered through the funnel member 123.

To fill and/or withdraw hydration medium from the interior cavity of the sleeve 104, a hydration medium delivery device, such as nozzle or needle 128, is inserted through opening 120 in ring 118, when one is present, and into opening 122 of the cap 108. The nozzle or needle 128 is then inserted into opening 112 of the insertion aid 106 and hydration medium is injected into and/or withdrawn from the interior cavity of the sleeve 104.

Figure 22:
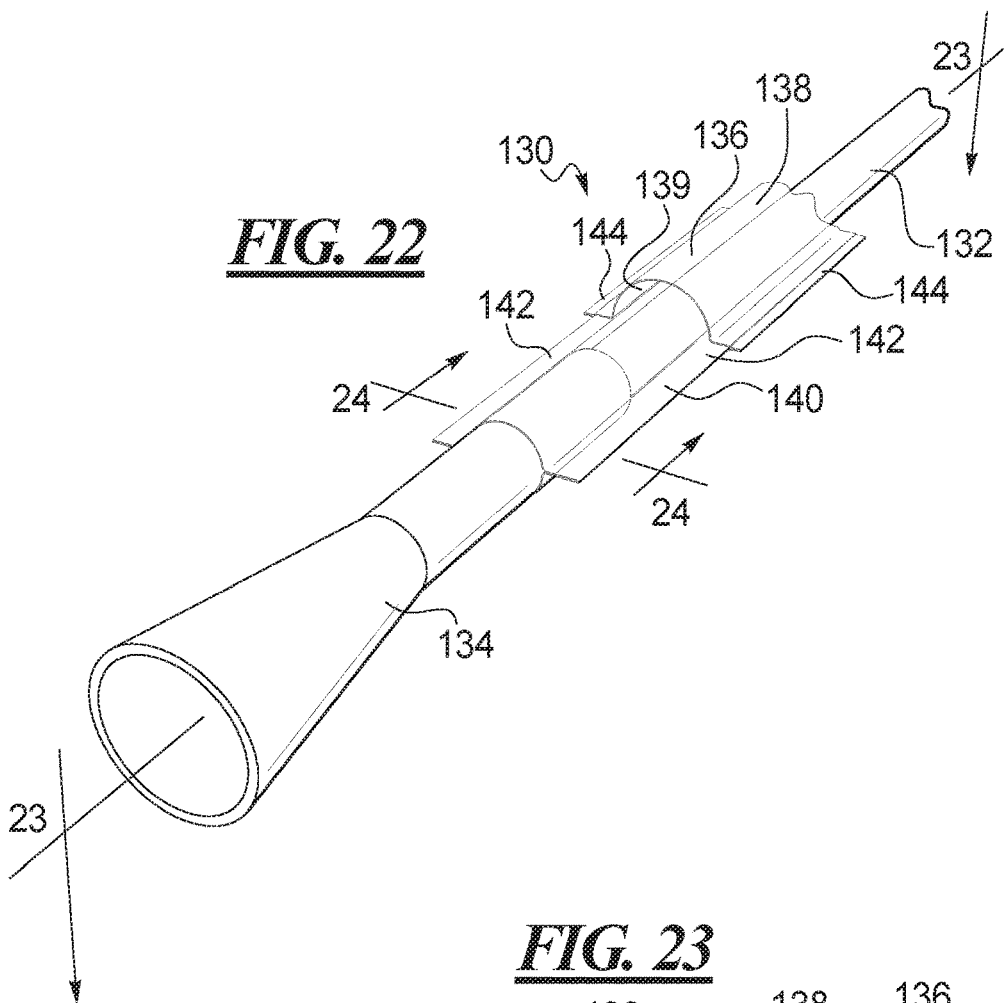
FIG. 22 is a perspective view of another embodiment of a catheter assembly in accordance with the present disclosure.
Figure 23:
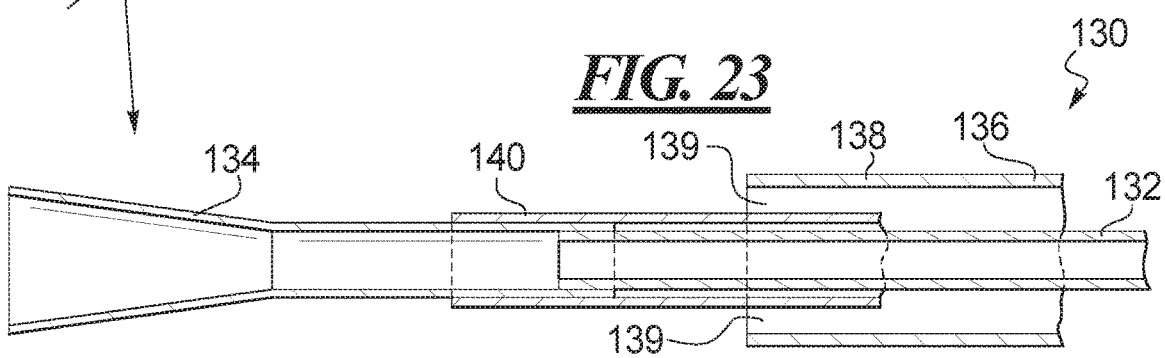
FIG. 23 is a cross-sectional view of the catheter assembly of FIG. 22.
Figure 24:
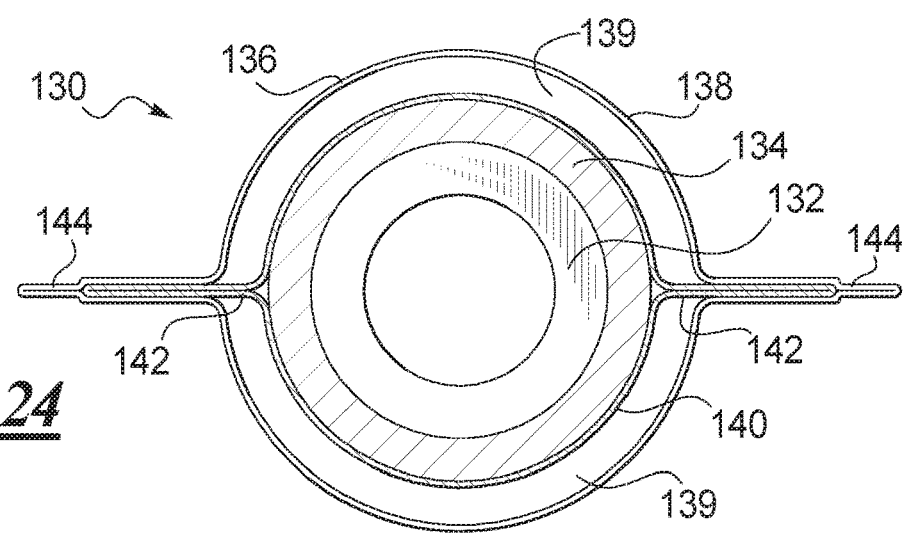
FIG. 24 is a cross-sectional view of the catheter assembly of FIG. 22.

FIGS. 22-24 illustrate another embodiment of a catheter assembly 130. The catheter assembly 130 includes a catheter 132 having drainage member 134 associated with the distal end portion of the catheter 132. The catheter assembly 130 also includes a sleeve 136 that may be used for the injection and/or withdrawal of hydration medium. The sleeve 136 may be a two-part sleeve that includes a proximal segment 138 and a distal segment 140. The proximal and distal segments 138 and 140 define one or more openings or passageways 139 therebetween that may be used to injection and/or withdraw hydration mediums. The proximal segment 138 of the sleeve 136 extends proximally to cover the catheter tube and, optionally, includes an introducer tip (not shown) associated therewith. The distal segment 140 of the sleeve may be attached to the drainage member 134.

As shown in FIGS. 22 and 24, the proximal segment 138 and the distal segment 140 of sleeve 136 may be attached to each other along the sides of each segment. For example, sides 142 of distal segment 140 of sleeve 136 may be attached to side 144 of proximal segment 138 of sleeve 136. In the illustrated embodiment, openings 139 are located on either side of the attachments. In other embodiments, the proximal and distal segments 138 and 140 may include a plurality of attachments spaced apart about the segments or there may be only one attachment. The proximal and distal sleeve segments 138 and 140 may be attached to each other in any suitable manner, such as be heat sealing, solvent bonding or adhesive.

To inject hydration medium into and/or withdraw hydration medium from the interior cavity of sleeve 136, a hydration medium delivery device, such as a nozzle or needle (not shown), may be inserted into or access opening(s) or passageway(s) 139.

FIGS. 25-27 illustrate another embodiment of a catheter assembly 150 wherein in the sleeve 152 includes openings or passageways 158 (FIG. 27) that may be used to inject and/or withdraw hydration medium to and from the interior cavity of the sleeve 152. The assembly 150 also includes a catheter 154 and a drainage member 156. FIG. 25 illustrates the catheter assembly 150 in the assembled configuration and FIG. 26 illustrates the catheter assembly 150 with the sleeve 152 separated so as to show the inner surface 160 of the sleeve 152. Referring to FIG. 26, a ply or layer of material 162 is attached to the inner surface 160 of the sleeve 152 such that opening or passageway 158 (FIG. 27) is defined between the inner surface 160 of the sleeve and the layer of material 162. For example, the layer 162 may be attached to the inner surface 160 of the sleeve 152 along side-edges 164*a* and 164*b*. The layer 162 may be attached to the sleeve 152 in any suitable manner, such as be heat sealing, solvent bonding or adhesive. The proximal edge 166*a* and the distal edge 166*b* are not attached to the inner surface 160 such that opening or passageway 158 (FIG. 27) is defined between the layer 162 and sleeve 152.

As shown in FIG. 27, the sleeve 152 may be attached to the drainage member 156. For example, a portion of the sleeve 168 and layer 162 may be attached to the drainage member 156. To inject hydration medium into and/or withdraw hydration medium from the interior cavity of sleeve 152, a hydration medium delivery device, such as a nozzle or needle (not shown), may be inserted into or access opening or passageway 158. Optionally, a one-way valve 157 may be located within or associated with passageway 158. The one-way valve may be attached to or molded with the drainage member 156. The hydration medium may be delivered through the one-way valve 157. The one-way valve will prevent hydration medium from exiting the sleeve 152.

FIGS. 28-30 illustrate another embodiment of a catheter assembly 170 wherein in the sleeve 172 includes openings or passageways 174 that may be used to inject and/or withdraw hydration medium from the interior cavity of the sleeve 172. The sleeve 172 includes one or more openings or passageways 174 therethrough. In the illustrated embodiment, the opening or passageway 174 is in the distal end of the sleeve. In other embodiments, the opening or passageway 174 may be in other locations of the sleeve, such as in the middle or proximal end of the sleeve.

To inject hydration medium into and/or withdraw hydration medium from the interior cavity of sleeve 172, a hydration medium delivery device, such as a nozzle or needle 176, may be inserted into or access opening or passageway 174. After the hydration medium has been injected and/or withdrawn and the nozzle or needle has been removed from the opening or passageway 174, a patch or layer 178 is placed over the opening or passageway 174 and attached to the sleeve 172 to cover opening or passageway 174. The patch or layer 178 may be attached by adhesive or any other suitable manner. Additionally, the patch 178 may be in the form of a flap wherein one end of the patch is connected to the sleeve 172. When the patch is a flap, the flap initially covers the passageway 174. The flap is peeled back for insertion of hydration medium, and then placed back over the passageway 174.

In an alternative embodiment, a needle may pierce the sleeve 172 and hydration medium is delivered through the needle. The needle may be removed and a patch 178 may be placed over the needle hole. The piercing and patch applying may be done with the aid of a location device.

FIG. 31 illustrate one embodiment of a mandrel or tube 180 that may be employed to inject hydration medium into and/or withdraw hydration medium from the interior cavity of a sleeve of a catheter assembly. The mandrel includes a proximal end portion 182 and a distal end portion 184. The distal end portion 184 includes an opening 186 for receiving a hydration medium. In the illustrated embodiment, the distal end portion 184 includes a hub 185 that may be connected to a hydration medium source. The proximal end portion 128 includes one or more openings 188 that are in fluid communication with opening 186 in the distal end portion 184. For example, the mandrel 180 may include a conduit or passageway (not shown) extending from the opening 186 to the one or more openings 188. In the illustrated embodiment, the opening 188 in the proximal end portion 182 includes a plurality of pin-holes. In other embodiments, the proximal end portion 182 may include a single opening.

Referring to FIGS. 32 and 33, the mandrel 180 may be inserted and advanced into the drainage member 192 of a catheter 194. The proximal end portion 182 and holes 188 may be aligned with eyelets or openings 196 of the catheter 194. Hydration medium may then be advanced through the mandrel 180 and out of the holes 188. The hydration medium then exits through the eyelets 196 of the catheter and into the interior cavity of the sleeve 198. Optionally, hydration medium may be extracted from the interior cavity of the sleeve 198. For example, the hydration medium may be extracted through the eyelets 196 of the catheter 194 and through the holes 188 in the mandrel 180.

FIG. 34 illustrates another method of forming a sleeved hydrophilic catheter assembly. In this method, a hydration medium 90 may be applied to the hydrophilic surface of the catheter tube 12. For example, the hydration medium 90 may be applied by dip coating, spraying, steaming or any other suitable application process. In the illustrated embodiment, the hydration medium 90 is in a hydration medium reservoir 92 and the catheter tube 12 is dipped into the hydration medium 90. Optionally, the hydration medium may be at an elevated temperature as described above. For example, the hydration medium 90 may be a liquid, aqueous solution, foam or gel at an elevated temperature. When the catheter tube 12 is dipped in the hydration medium 90, the catheter tube 12 may be allowed to dwell in the hydration medium 90 for a selected period of time. The selected period of time may be sufficient to fully or partially hydrate/activate the hydrophilic surface of the catheter. The catheter 12 is then removed from the hydration medium 90. When the hydration medium is a gel, the gel may form a gel coating that covers at least a portion of the hydrophilic surface of the catheter tube and preferably covers the entire hydrophilic surface. The sleeve 22 is then assembled around the catheter tube 12 and, optionally, an inserter aid and protective cap is assembled with the sleeve. The sleeve may be any of those discussed above or any other suitable sleeve. The catheter assembly is placed in a package, such as any of those discussed above. For example, the package may include a vapor hydration atmosphere and the sleeve may be vapor permeable, as discuss above. The package may then be submitted to sterilizing radiation, such as e-beam or gamma radiation. When a gel is used as the hydration medium, the gel may be of the type that liquefies or becomes less viscous when exposed to radiation.

Figure 35:
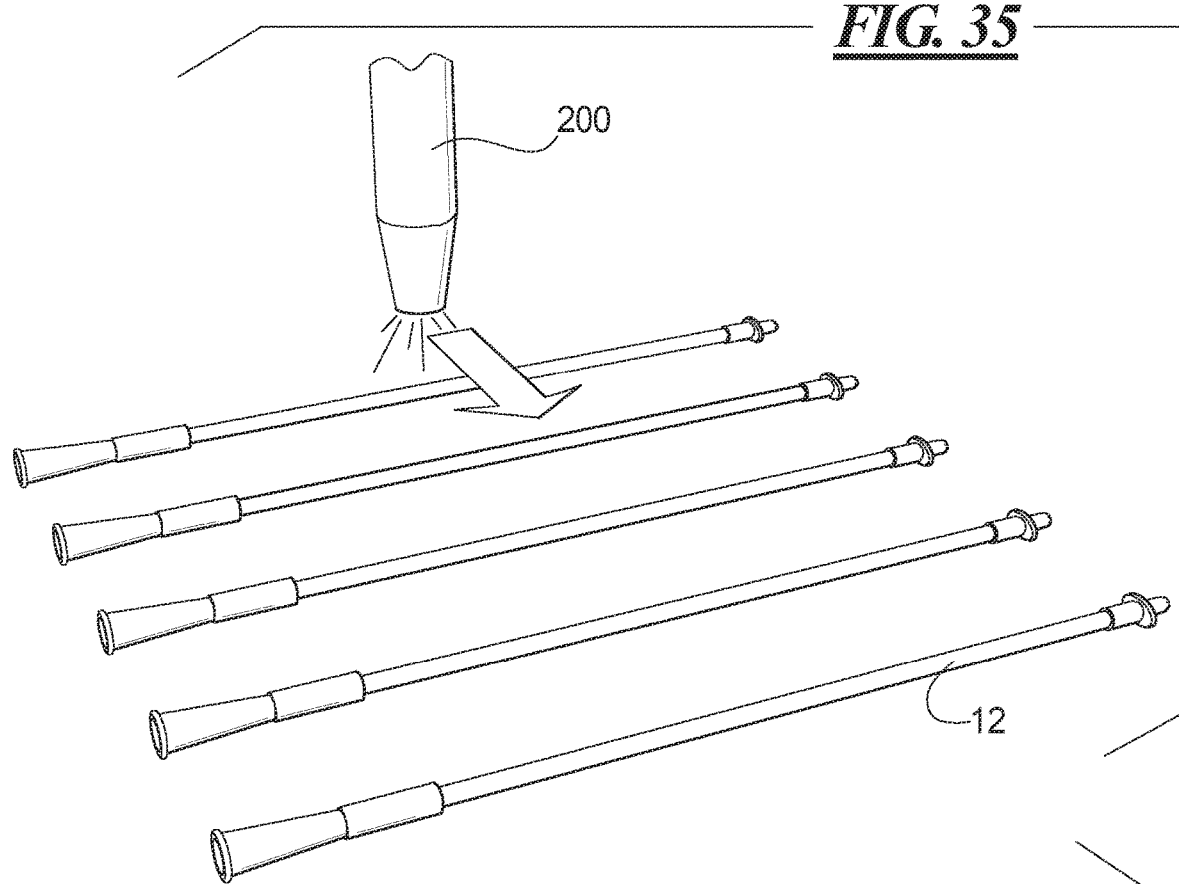
FIG. 35 is a perspective view of one embodiment of a system and method of making a hydrophilic catheter assembly.

FIG. 35 illustrates another embodiment of a system and method for applying a hydration medium to a catheter. The system may include a sprayer 200 that sprays hydration medium on to the hydrophilic surface of the catheter tubes 12.

Figure 36:
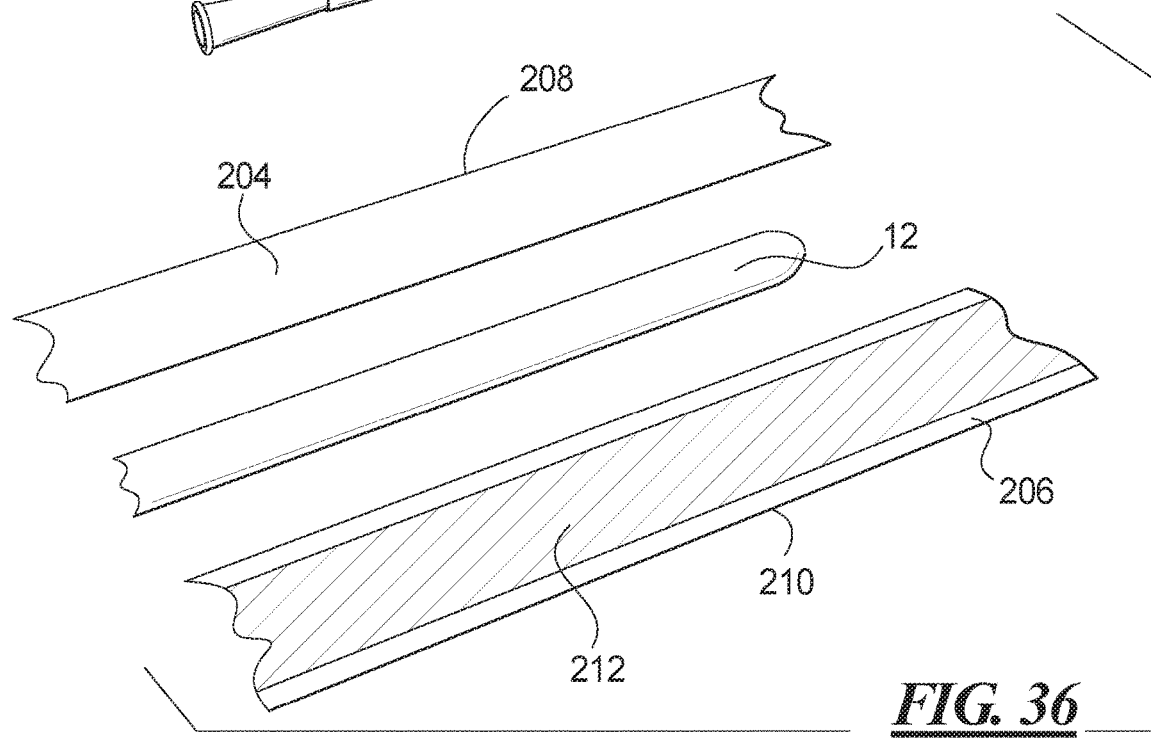
FIG. 36 is a perspective view of another embodiment of a catheter assembly.

FIG. 36 illustrates another hydrophilic catheter product and method of forming the same. The catheter product includes a top sheet 204 and a bottom sheet 206 that are sealed or attached together along their peripheral edges 208 and 210, respectively, to from the sleeve surrounding the catheter tube 12. At least one of the inner surfaces of the top sheet 204 and the bottom sheet 206 is coated with a hydration medium 212, such as a hydration gel that releases hydration liquid. The hydration medium may be applied in any sufficient manner. For example, the hydration medium may be rolled, sprayed or brushed on the sheet. After the top and bottom sheets are attached to each other, the gel is activated to release the hydration liquid.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method of making a ready-to-use urinary catheter product, wherein the product includes a catheter assembly with a sleeve defining an inner cavity and a urinary catheter having a catheter tube located within the inner cavity of the sleeve, the catheter tube having an outer hydrophilic surface, an insertion aid at a distal end of the sleeve configured for passage of the catheter tube therethrough during catheterization, a protective cap and the protective ca includes a passageway, the method comprising: inserting the hydration medium delivery device through the passageway of the protective cap and engaging a hydration medium delivery device with an aperture of the insertion aid; delivering a hydration medium from the hydration medium delivery device, wherein the hydration medium flows from the delivery device through the insertion aid and immediately into the inner cavity of the sleeve where the hydration medium is loose and hydrates the outer hydrophilic surface of the catheter tube; and placing the catheter assembly with the hydrated hydrophilic surface in an outer package.

2. The method of claim 1, further including withdrawing at least some of the hydration medium from the inner cavity of the sleeve.

3. The method of claim 1, wherein the insertion aid defines the aperture in communication with the inner cavity of the sleeve, and wherein the step of engaging the hydration medium delivery device with the insertion aid comprises engaging the hydration medium delivery device with the aperture and the step of delivering hydration medium through the insertion aid and into the inner cavity of the sleeve comprises delivering hydration medium through the aperture in the insertion aid.

4. The method of claim 3, wherein the aperture is moveable between a closed configuration and an open configuration.

5. The method of claim 4, further including moving the aperture into the open configuration prior to delivering the hydration medium through the insertion aid.

6. The method of claim 4, wherein delivering the hydration medium moves the aperture from the closed configuration to the open configuration.

7. The method of claim 4, wherein the insertion aid includes a plurality of petals defining the aperture.

8. The method of claim 7, wherein the petals move to define the open configuration of the aperture.

9. The method of claim 3, wherein the insertion aid has a proximal end and a distal end, the insertion aid including an introducer tip at the proximal end thereof, and the aperture being located in the introducer tip.

10. The method of claim 9, wherein the aperture is configured to have the catheter tube advanced therethrough during catheterization.

11. The method of claim 3, wherein the insertion aid includes a barrel portion and the aperture is located in the barrel portion.

12. The method of claim 11, wherein a portion of the sleeve covers the aperture.

13. The method of claim 1, wherein the catheter product includes a protective cap covering the insertion aid.

14. The method of claim 1, wherein the passageway of the protective cap includes a funnel-shaped member in communication with the aperture of the insertion aid.

15. The method of claim 1, wherein the protective cap includes a grasping ring defined by a band and the band includes an opening therethrough for allowing the passage of the hydration medium delivery device.

16. The method of claim 1, wherein engaging the hydration medium delivery device with the insertion aid comprises docking the insertion aid to a nozzle of a hydration medium delivery system.

17. The method of claim 2, wherein withdrawing at least some of the hydration medium comprises withdrawing at least some of the hydration medium through the insertion aid and the hydration medium delivery device.

18. The method of claim 1, wherein the hydration medium comprises a hydration foam.

* * * * *